(12) United States Patent
Henriksen

(10) Patent No.: US 11,912,791 B2
(45) Date of Patent: Feb. 27, 2024

(54) SOLUTION PHASE ROUTES FOR WNT HEXAPEPTIDES

(71) Applicant: WNTRESEARCH AB, Malmö (SE)

(72) Inventor: Dennis Henriksen, Malmö (SE)

(73) Assignee: WNTRESEARCH AB, Malmö (SE)

( * ) Notice: Subject to any disclaimer, the term of this patent is extended or adjusted under 35 U.S.C. 154(b) by 13 days.

(21) Appl. No.: 17/267,764

(22) PCT Filed: Aug. 19, 2019

(86) PCT No.: PCT/EP2019/072122
§ 371 (c)(1),
(2) Date: Feb. 10, 2021

(87) PCT Pub. No.: WO2020/038878
PCT Pub. Date: Feb. 27, 2020

(65) Prior Publication Data
US 2021/0171575 A1    Jun. 10, 2021

(30) Foreign Application Priority Data

Aug. 20, 2018 (EP) .................................... 18189699

(51) Int. Cl.
*C07K 7/06* (2006.01)
*C07K 5/083* (2006.01)

(52) U.S. Cl.
CPC ................. *C07K 7/06* (2013.01); *C07K 5/081* (2013.01)

(58) Field of Classification Search
CPC .......... C07K 7/06; C07K 5/081; C07K 14/47; C07K 1/02; C07K 1/10; C07K 1/16; C07K 1/30; C07K 1/36; C07K 5/06; C07K 5/10; Y02P 20/55; C07B 2200/13
See application file for complete search history.

(56) References Cited

U.S. PATENT DOCUMENTS

| 7,439,222 B2 | 10/2008 | Guinn et al. |
| 2017/0368158 A1 | 12/2017 | Vescovi et al. |

FOREIGN PATENT DOCUMENTS

| EP | 381340 A | * 8/1990 | ................. A61P 3/04 |
| WO | WO-2006130082 A1 | * 12/2006 | .......... C07K 14/475 |
| WO | WO 2016/092378 A1 | 6/2016 | |
| WO | WO 2016/154580 A1 | 9/2016 | |

OTHER PUBLICATIONS

Isidro-Llobet et al (Chem.Rev., 2009, 109, 2455-2504) (Year: 2009).*
Bruckdorfer et al., "From Production of Peptides in Milligram Amounts for Research to Multi-Tons Quantities for Drugs of the Future", Current Pharmaceutical Biotechno, 2004, 5(1): 29-43.
Hidaka et al., "Disulfide Linkages in a Heat-Stable Enterotoxin (STp) Produced by a Porcine Strain of Enterotoxigenio *Escherichia coli*", Bulletin of the Chemical Society of Japan, 1988, 61(4): 1265-1271.
Neumann et al., "Prevention of aspartimide formation during peptide synthesis using cyanosulfurylides as carboxylic acid-protecting groups", Nature Communications, 2020, 11:982, 10 pages.
Takahashi et al., "Novel diphenylmethyl-Derived Amide Protecting Group for Efficient Liquid-Phase Peptide Synthesis: Ajiphase", Organic Letters, 2012, 14(17): 4514-4517.
Tsuda et al., "Solution-Phase Peptide Synthesis", Ch. 6 in Amino Acids, Peptides and Proteins in Organic Chemistry, 2011, 3: 203-251.

* cited by examiner

*Primary Examiner* — Sudhakar Katakam
(74) *Attorney, Agent, or Firm* — James S. Keddie; Bozicevic, Field & Francis LLP

(57) ABSTRACT

The present disclosure relates generally to the field of polypeptide synthesis, and more particularly, to the solution phase synthesis of the Wnt hexapeptide Foxy-5 and protected derivatives and peptide fragments thereof.

6 Claims, 11 Drawing Sheets

Specification includes a Sequence Listing.

SOLUTION PHASE ROUTES FOR WNT HEXAPEPTIDES

CROSS-REFERENCE TO RELATED APPLICATIONS

This application is a § 371 national phase of International Application No. PCT/EP2019/072122, filed on Aug. 19, 2019, which claims the benefit of European Patent Application No. 18189699.4, filed on Aug. 20, 2018, which applications are incorporated by reference herein.

FIELD OF THE INVENTION

The present disclosure relates generally to the field of polypeptide synthesis, and more particularly, to the solution phase synthesis of Wnt hexapeptide Foxy-5. The present disclosure further relates to the solution phase synthesis of novel tri-, tetra- and pentapeptides.

BACKGROUND OF THE INVENTION

Foxy-5 is a formylated, Wnt5a-derived hexapeptide and Wnt-5a mimetic with potential anti-metastatic activity currently in development as a drug candidate for the prevention of tumor spread in several common forms of cancer.

Foxy-5 has the amino acid sequence For-Met-Asp-Gly-Cys-Glu-Leu-OH (SEQ_ID NO 1, FIG. 1). Upon intravenous administration, Foxy-5 binds to and activates the wnt-5a receptors, Frizzled-2 and -5, which activates wnt-5a-mediated signaling. Increased wnt-5a signaling may inhibit endothelial tumor cell migration and invasion.

Foxy-5 is intended to compensate for the deficiency of protein Wnt-5a in tumor tissue noted in patients with colon cancer, in order to reduce the risk of metastasis. A sub-analysis from a recent retrospective study of patients with colorectal cancer in stage Ill, shows that the proportion of patients with low expression of Wnt 5a is significantly higher than observed in previous studies in patients with stage II colorectal cancer (CRC). Patients with CRC stage Ill tumors differ from stage II mainly by the presence of tumor cells in lymph nodes adjacent to the primary tumor, thereby being more aggressive and faster progressing. A low level of Wnt-5a has been observed in close to 70 percent of patients in stage Ill, compared with approximately 45 percent of patients with less advanced tumor stages. This supports the hypothesis that the Wnt-5a level significantly influences the course of disease.

Based on a completed Phase 1b study with Foxy-5 aimed at documenting the drug candidate's safety profile, pharmacokinetics and dose determination for Phase 2, Foxy-5 is now posed for a Phase 2 clinical trial study, where treatment in colon cancer patients will be initiated at the time of diagnosis, before surgery has been conducted. The treatment is intended to last for a maximum of 12 weeks, or until the initiation of chemotherapy.

Foxy-5 and a method for its preparation are described in International Pat. Publication No. WO06130082 A1. The active pharmaceutical ingredient (API) for the preclinical and clinical studies conducted so far has been produced by classical solid phase peptide synthesis (SPPS), whereby Foxy-5 is produced by a linear 1+1+1+1+1+1 route, see FIG. 2. The sequence For-Met-Asp-Gly-Cys-Glu-Leu-OH is thus assembled on a 2-chlorotrityl resin carrying the C-terminal amino acid Leu using the Fmoc-strategy (Fmoc=fluorenylmethyloxycarbonyl). Synthesis is performed in an SPPS reactor and consists of alternating coupling, acetylation, and N-α-deprotection procedures. The coupling is performed in DMF (N,N-dimethylformamide) or DMF/DCM (dichloromethane) as solvent. It consists of coupling the N-α-protected amino acid derivative to the preceding amino acid in the presence of an activating reagent and a base, if necessary. Formic acid is coupled as an active ester without activating agents.

If the coupling is not complete, it can be continued or the procedure can be repeated. In order to avoid the formation of deletion sequences as by-products, a systematic acetylation procedure (capping) is performed after the coupling step or, if recoupling is performed after the recoupling steps, using DMF, acetic anhydride, and pyridine.

Acetylation is followed by an N-α-deprotection procedure which consists of washing the resin with DMF, cleaving the Fmoc-group with piperidine in DMF, and subsequent washings with DMF. In case of incomplete cleavage, the N-α-deprotection procedure as described above can be repeated. For each single step, the solvents and/or reagents are added, and the reaction mixture is stirred and then filtered to remove solvents and/or reagents from the resin.

Coupling, acetylation, and N-α-deprotection procedures are repeated until the resin carries the complete peptide sequence For-Met-Asp-Gly-Cys-Glu-Leu-OH. After the final coupling of the formic acid active ester, no acetylation is performed. The SPPS is completed by washing the peptide resin with DMF and IPA and subsequent drying under reduced pressure.

Cleavage of the peptide from the resin and concomitant cleavage of the side-chain protecting groups is accomplished by treatment of the peptide resin with TFA in the presence of suitable scavengers (e.g. water and EDT). Subsequently, the crude peptide obtained is purified by two-dimensional preparative HPLC on a reversed phase column with ACN gradient elution (formic acid and acetic acid systems).

Pooled fractions with adequate purity are lyophilized. The lyophilizate is analyzed by HPLC and optionally repurified by two-dimensional preparative HPLC as outlined above in case of non-compliance with the set criteria for purity.

The SPPS approach outlined above has generated sufficient material for the preclinical and early clinical research, but for further clinical studies and eventual commercial purposes, a synthesis better suited for large scale synthesis is required, by which the cost of goods can be reduced and larger batches of Foxy-5 can be made available.
There is thus a need for a reliable route of synthesis which can provide Foxy-5 in multi-kg scale, both for further clinical trial supply and eventual commercial purposes.

ABBREVIATIONS

Figure 1:
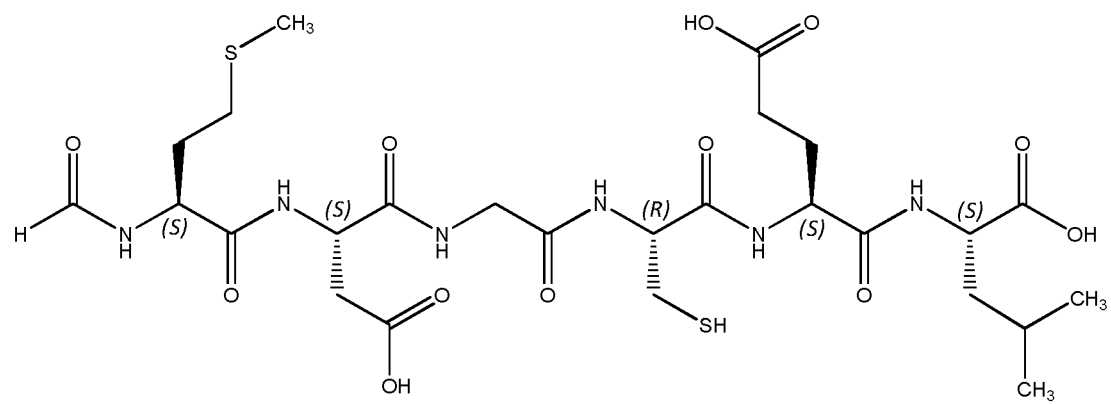
FIG. 1 shows the chemical structure of Foxy-5. Foxy-5 is a linear peptide consisting of six amino acids with a formylated N-terminus. All optically active amino acid residues are in the L-configuration. The molecular formula of Foxy-5 is $C_{26}H_{42}N_6O_{12}S_2$, and the molecular mass is 694.8 g/mol (average mass).
Figure 2:
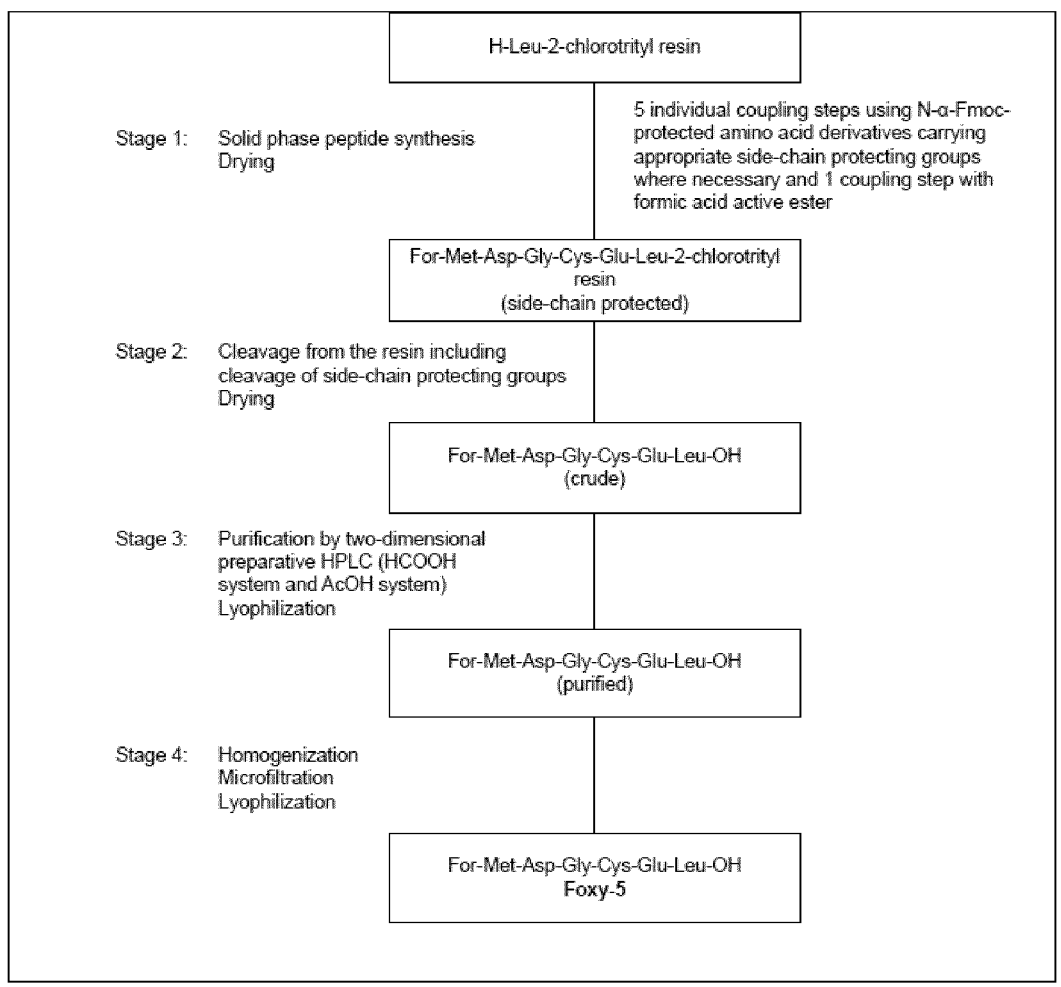
FIG. 2 shows the synthetic scheme for the SPPS route to Foxy-5.
Figure 3:
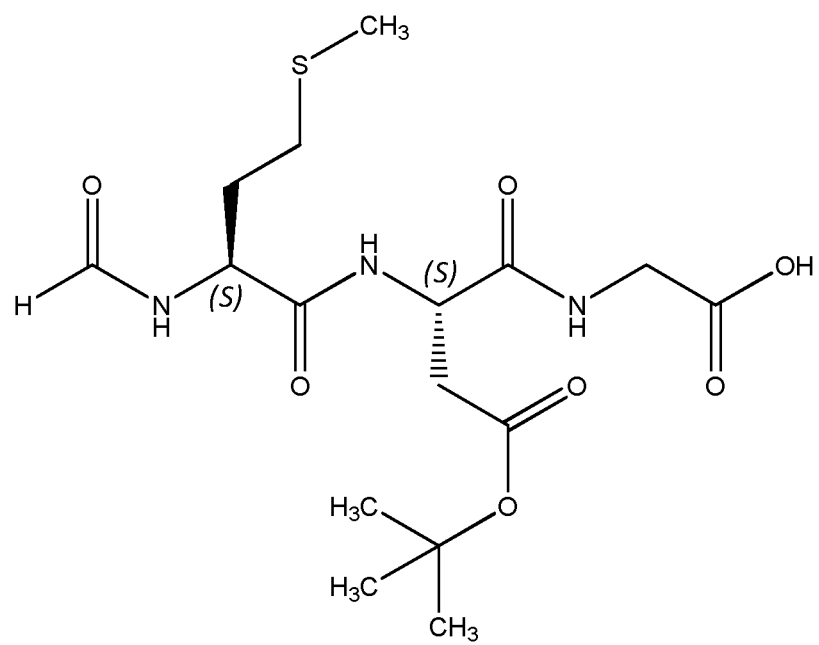
FIG. 3 shows the chemical structure of Key Tripeptide 1 (KT-1), ie For-Met-Asp(OtBu)-Gly (top figure) and Key Tripeptide 1* (KT-1*), ie Fmoc-Met-Asp(OtBu)-GlyAll optically active amino acid residues are in the L-configuration. The molecular formula of KT-1 is $C_{16}H_{27}N_3O_7S$, and the molecular mass is 405 g/mol (average mass).
Figure 3:
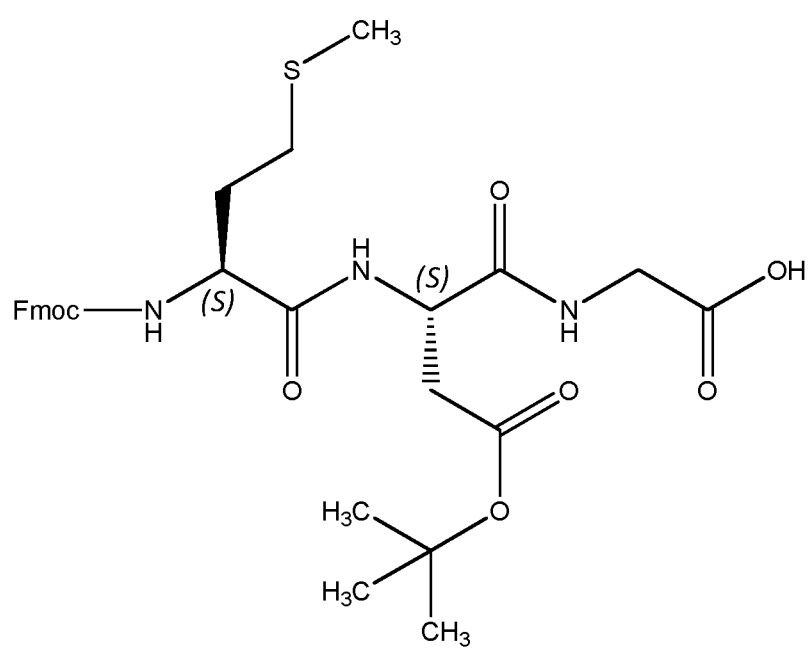
Figure 4:
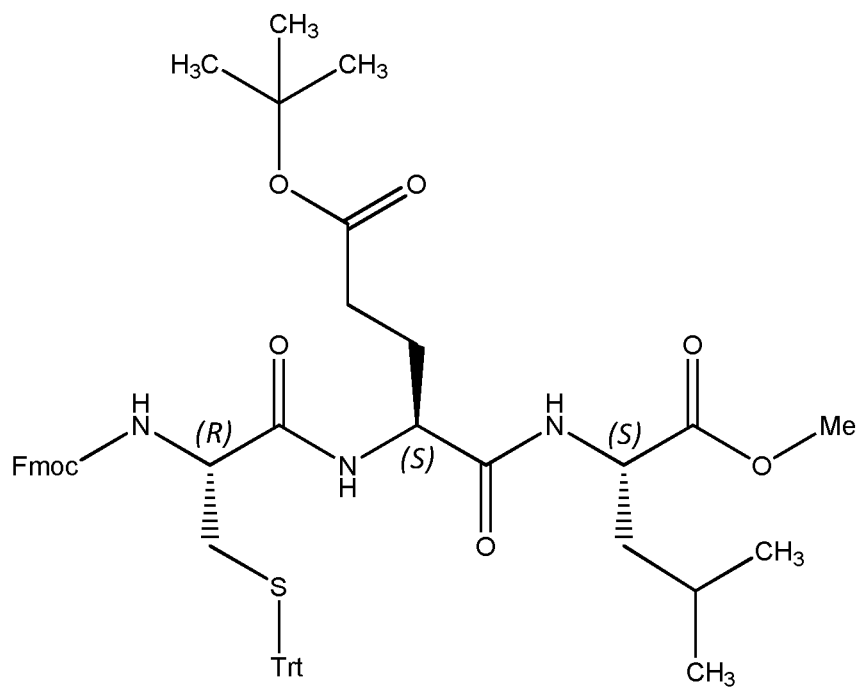
FIG. 4 shows the structure of Key Tripeptide 2 (KT-2), Fmoc-Cys(Trt)Glu(OtBu)-Leu-OMe (top) and Key Tripeptide 2* (KT-2*), Fmoc-Cys(Trt)Glu(OtBu)-Leu-O-tert-Bu (bottom)
Figure 4:
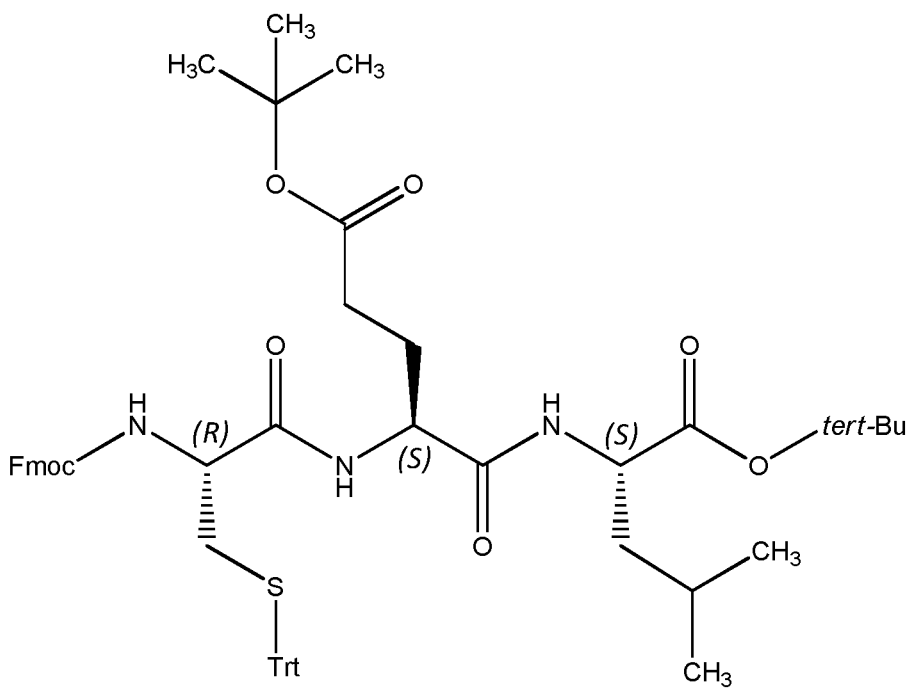

Fmoc=Fluorenylmethoxycarbonyl
Boc=tert-Butyloxycarbonyl
For=Formyl
Trt=Triphenyl methyl (Trityl)
Cbz=carboxybenzyl
DCHA=dicyclohexylamine
tBu=tert-Butyl
THF=Tetrahydrofuran
DMF=N,N-Dimethylformamide
TEA=Triethylamine
Bn=Benzyl
TFA=Trifluoroacetic acid
TIS=Triisopropylsilane
HOBt=1-Hydroxybenzotriazole
HOSu=N-Hydroxysuccinimide
DCM=Dichloromethane
HOAt=1-Hydroxy-7-azabenzotriazole
EDAC, HCl=1-Ethyl-3-(3'-dimethylaminopropyl)carbodiimide, HCl
DIPEA=Diisopropylamine
DIPE=Diisopropylether
DBU=1,8-Diazabicyclo[5.4.0]undec-7-ene
Amino Acid Abbreviations:
Met=Methionine
Asp=Asparagine
Gly=Glycine
Cys=Cysteine
Glu=Glutamic acid
Leu=Leucine
Foxy-5=For-Met-Asp-Gly-Cys-Glu-Leu

SUMMARY OF THE INVENTION

The instant disclosure provides several solution-phase methods for preparing the formylated hexa peptide known as "Foxy-5" (i.e. For-Met-Asp-Gly-Cys-Glu-Leu-OH), and also various tri-, tetra-, penta- and hexapeptide fragments thereof, including protected derivatives thereof. The methods provided herein possess several advantages over traditional solid phase syntheses, including but not limited to, low raw materials costs, ease of purification of process intermediates, ease of fragment assembly, high chiral purity, and adaptability to commercial scale-up, among others, to be described in greater detail below.

It is thus a primary objective of the present invention to provide a scalable route of synthesis for Foxy-5. It is a further objective to identify and characterize suitable Key intermediates for said scalable route of synthesis for the purpose of later GMP (Good Manufacturing Practice) manufacture of the drug substance.

In view of the cost of goods and cumbersome scalability normally associated with solid phase chemistry, the focus has been on developing solution phase chemical routes. The instant disclosure thus provides solution phase methods for preparing Foxy-5, or intermediates and precursors thereof, using fragment coupling strategies.

Three different approaches have been tested:
A 2+2+2 coupling strategy, whereby three dipeptides are coupled to form the final hexapeptide,
A 3+3 coupling strategy, whereby two tripeptides are coupled,
A 4+1+1 coupling strategy, whereby a tetrapeptide is sequentially elongated, and
A 3+1+1+1 coupling strategy, whereby a tripeptide is sequentially elongated.

In the 2+2+2 approach, the main chain of Foxy-5 is assembled by coupling of three independent key dipeptide fragments, KD-1, KD-2 and KD-3. Three different approaches were devised, a, b and c, see FIG. 5, FIG. 6 and FIG. 6a. The solution phase fragment synthesis of these three dipeptides was followed by formation of the hexapeptide in a convergent manner. The protective group strategy in the 2+2+2 approach was based on either hydrogenolysis of N-terminal protecting groups (Cbz), or base-catalyzed deprotection of N-terminal protecting groups (Fmoc) of fragments and involved the use of acid-labile protective group on the side chains. In addition, all intermediates could be accessed by solution phase chemistry. For all three 2+2+2 approaches, the Met N-formyl group is introduced in the final stage of the synthesis after all three dipeptide fragments have been coupled.

In the 3+3 approach, the main chain of Foxy-5 is assembled by solution phase fragment coupling of two tripeptide fragments. In one version of the 3+3 approach, using Key Tripeptide KT-1 and KT-2 (FIG. 7), the formyl group is introduced early on, i.e. in the synthesis of the tripeptide fragment KT-1. In a second version of the 3+3 approach, the formyl group is first introduced after the hexapeptide backbone has been established through coupling of two different tripeptide fragments, KT-1* and KT-2* (FIG. 7a).

In a first aspect of the present invention there is provided a novel tripeptide Met-Asp-Gly and its protected derivatives, For-Met-Asp(OtBu)-Gly (Key tripeptide-1, KT-1) and Fmoc-Met-Asp(OtBu)-Gly (Key tripeptide-1*, KT-1*).

In a second aspect of the present invention there is provided a novel tripeptide Cys-Glu-Leu and its protected derivatives, Fmoc-Cys(Trt)Glu(OtBu)-Leu-O-Me (Key tripeptide-2, KT-2) and Fmoc-Cys(Trt)Glu(OtBu)-Leu-OtBu (Key tripeptide-2*, KT-2*).

In a third aspect of the present invention there is provided a method of production for the hexapeptide Foxy-5 in protected form, based on the coupling of the novel tripeptide derivatives KT-1 and KT-2, alternatively based on the coupling of the novel tripeptide derivatives KT-1* and KT-2*, which coupling may (dependent on actual route) be followed either by global deprotection or N-deprotection followed by N-formylation and final side chain deprotection to furnish the desired hexapeptide Foxy-5.

In the 3+1+1+1 approach, the main chain of Foxy-5 is assembled by sequential solution phase coupling of either tripeptide fragment KT-2 or KT-2* with protected derivatives of amino acids Gly, Asp and Met to form either Foxy-5 or the hexapeptide Met-Asp-Gly-Cys-Glu-Leu-OH in protected form. Dependent on the actual route, global deprotection or N-deprotection followed by N-formylation and final side chain deprotection furnishes the desired hexapeptide Foxy-5.

In a fourth aspect of the present invention there is provided a method of production for the hexapeptide Foxy-5 in protected form, based on the sequential coupling of the novel tripeptide derivatives KT-2 or KT-2* with protected derivatives of amino acids Gly, Asp and Met, which sequence of couplings may be followed (depending on specific starting tripeptide) by global deprotection or N-deprotection followed by N-formylation and final side chain deprotection furnishes the desired hexapeptide Foxy-5.

DETAILED DESCRIPTION

As mentioned in the summary hereinabove four different solution phase approaches for assembling the Foxy-5 hexapeptide sequence were devised, a 2+2+2 route (three versions), a 3+3 route (two versions), a 4+1+1 route and a 3+1+1+1 route (2 versions). The strategies are discussed in more detail in the following.

2+2+2 Coupling Strategy

Figure 5:
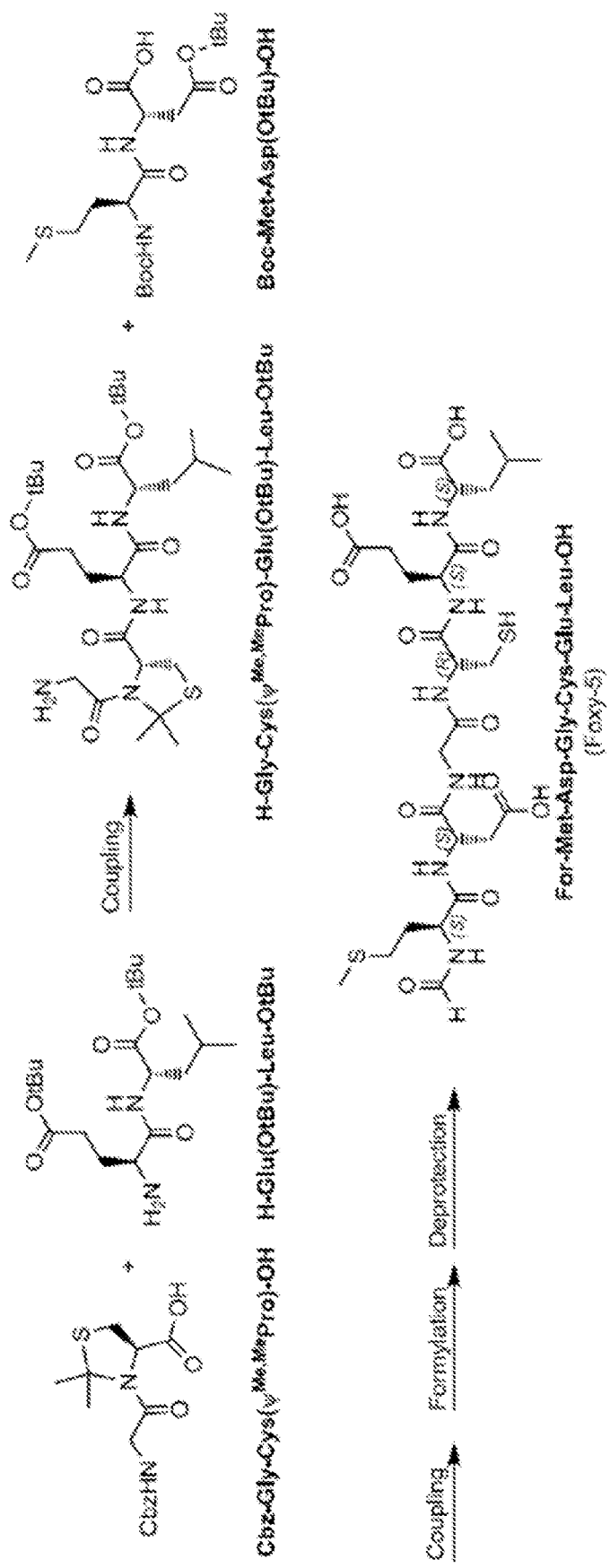
FIG. 5 illustrates a 2+2+2 strategy for the formation of Foxy-5 based on an acid-labile protection group strategy.

2+2+2 Route A (FIG. 5)

The synthesis of the first key dipeptide KD-1a (Boc-Met-Asp(OtBu)-OH) starts with the coupling of commercially available Boc-Met-OH and HAsp(OtBu)-OMe. The resulting dipeptide Boc-Met-Asp(OtBu)-OMe is then deprotected selectively at the C-terminus.

The second key dipeptide, KD-2a (Cbz-Gly-Cys($\psi^{Me,Me}$Pro)-OH) is then prepared by formation of cysteine acetonide H-Cys($\psi^{Me,Me}$Pro)-OH from H-Cys-OH and acetone, followed by coupling with the succinimide ester Cbz-Gly-OSu.

The synthesis of the third dipeptide KD-3a, (H-Glu(OtBu)-Leu-OtBu) involves the coupling of commercially available starting materials Cbz-Glu(OtBu)-OH and H-Leu-OtBu. Subsequent Cbz-deprotection by hydrogenation over Pd/C yields the intermediate dipeptide H-Glu(OtBu)-Leu-OtBu.

Synthesis of Foxy-5 by Route A from the three key dipeptides KD-1a, KD-2a and KD-3a is finally initiated by coupling dipeptides KD-2a Cbz-Gly-Cys($\psi^{Me,Me}$Pro)-OH and KD-3a H-Glu(OtBu)-Leu-OtBu, giving the tetrapeptide Gly-Cys($\psi^{Me,Me}$Pro)-Glu(OtBu)-Leu-OtBu (SEQ_ID NO 5) after deprotection. Dipeptide KD-1a, Boc-Met-Asp(OtBu)-OH is then coupled with the tetrapeptide Gly-Cys($\psi^{Me,Me}$Pro)-Glu(OtBu)-Leu-OtBu in the presence of standard coupling reagents. Global deprotection is performed by treatment of the resulting protected hexapeptide with a strong acid. Subsequent formylation yields then the target compound Foxy-5 in crude form.

Figure 6:
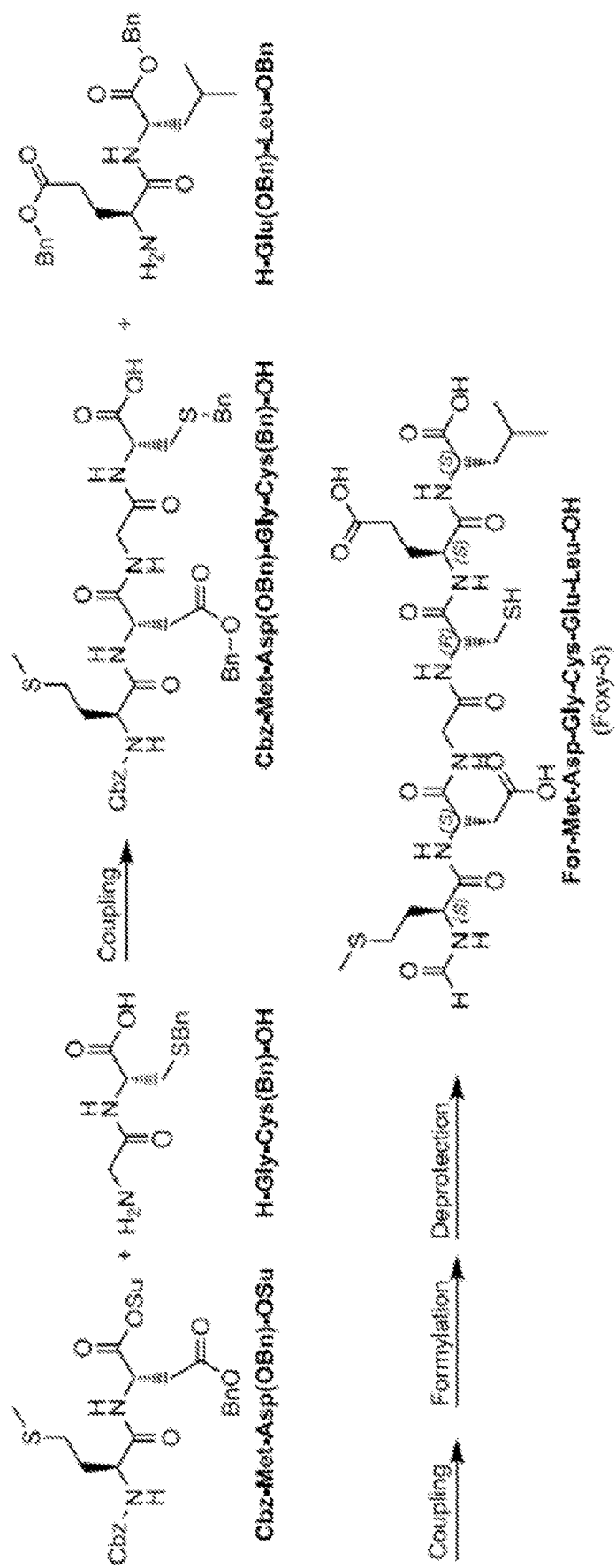
FIG. 6 illustrates a 2+2+2 strategy for the formation of Foxy-5 based on a hydrogenolytic protection group strategy.

2+2+2 Route B (FIG. 6)

The synthesis of the first key dipeptide KD-1b (Cbz-Met-Asp(OBn)-OSu) involves the formation of succinimide ester Cbz-Met-OSu from the corresponding methionine derivative. Coupling of the activated ester with commercially available H-Asp(OBn)-OH under basic conditions yields the Cbz-Met-Asp(OBn)-OH dipeptide that is then also activated with HOSu, leading to the first dipeptide KD-1, Cbz-Met-Asp(OBn)-OSu.

For the second key dipeptide, KD-2b (H-Gly-Cys(Bn)-OH) cysteine is initially benzyl-protected on the side-chain yielding H-Cys(Bn)-OH. Commercially available succinimide-activated glycine building block Boc-Gly-OSu is then coupled to the benzyl-protected cysteine building block to yield the desired dipeptide KD-2b, H-Gly-Cys(Bn)-OH after Boc-deprotection.

The third key dipeptide, KD-3b (H-Glu(OBn)-Leu-OBn) is formed by coupling of the activated ester Boc-Glu(OBn)-OSu and commercially available H-Leu-OBn.

Synthesis of Foxy-5 by Route B from the three dipeptide fragments KD-1b, KD-2b and KD-3b is finally initiated by coupling of protected key dipeptides KD-1b (Cbz-Met-Asp(OBn)-Osu) and KD-2b (H-Gly-Cys(Bn)-OH) to yield protected tetrapeptide Cbz-Met-Asp(OBn)-Gly-Cys(Bn)-OH (SEQ_ID NO 12) which is subsequently coupled with KD-3b (H-Glu(OBn)-Leu-OBn) to yield Cbz-Met-Asp(OBn)-Gly-Cys(Bn)-Glu(OBn)-Leu-OBn (SEQ_ID NO 13). This protected hexapeptide is then globally deprotected by hydrogenation over Pd/C, yielding the hexapeptide Met-Asp-Gly-Cys-Glu-Leu-OH (SEQ_ID NO 14), which in a last chemical step is formylated to give the desired hexapeptide Foxy-5 in crude form.

It is noted that the tetrapeptides Gly-Cys-Glu-Leu-OH (SEQ_ID NO 8) and Met-Asp-Gly-Cys-OH (SEQ_ID NO 11) and their two protected derivatives, Gly-Cys($\psi^{Me,Me}$Pro)-Glu(OtBu)-Leu-OtBu (SEQ_ID NO 5) and Cbz-Met-Asp(OBn)-Gly-Cys(Bn)-OH (SEQ_ID NO 12) described herein, are novel compounds. Likewise, the protected hexapeptide Cbz-Met-Asp(OBn)-Gly-Cys(Bn)-Glu(OBn)-Leu-OBn (SEQ_ID NO 13), is a novel compound.

Figure 6A:
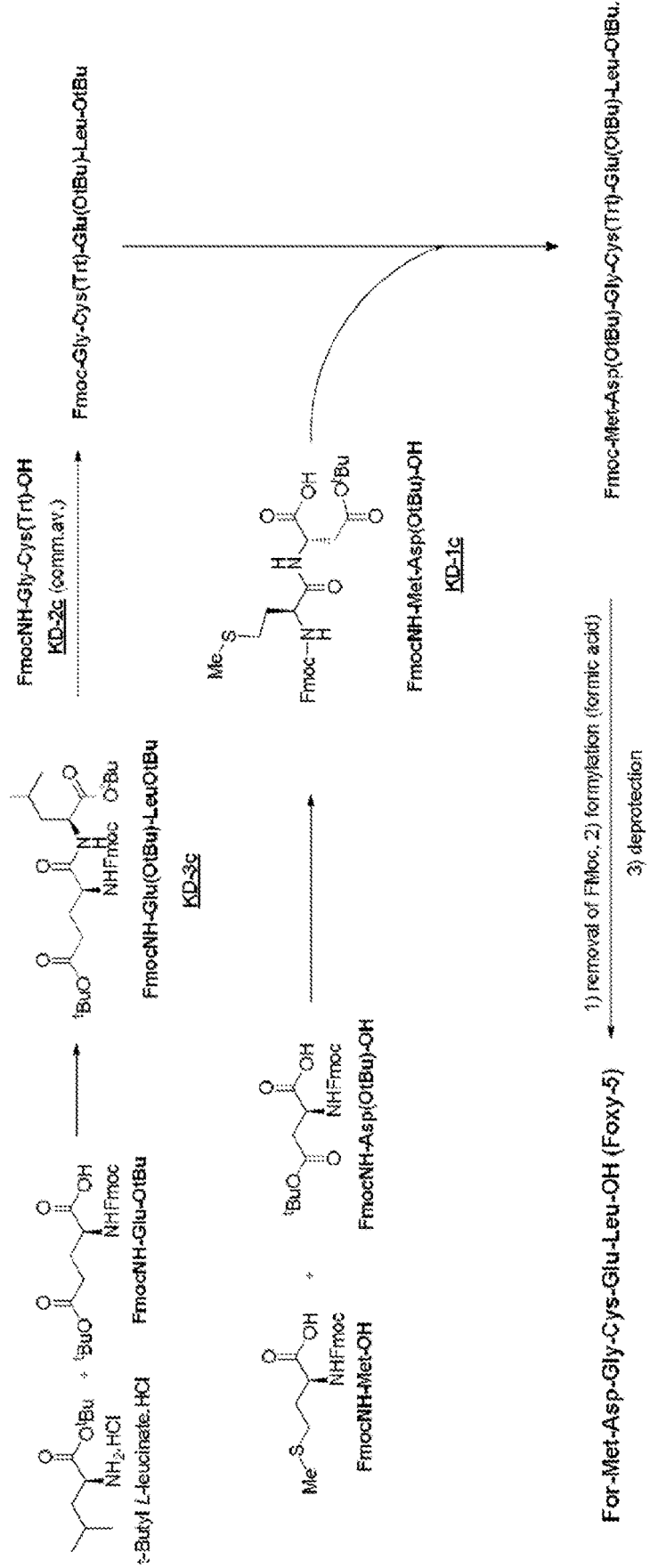
FIG. 6a illustrates a 2+2+2 strategy for the formation of Foxy-5 based on a base-labile protection group strategy.

2+2+2 Route C (FIG. 6a)

The synthesis of the first key dipeptide KD-1c, Fmoc-Met-Asp(OtBu)-OH was performed by coupling of commercially available Fmoc-Met-OH and H-Asp(OtBu)-OH with dicyclohexyl carbodiimide (DCC).

The synthesis of the second key dipeptide KD-2c, Fmoc-Gly-Cys(Trt)-OH, was obviated as the protected dipeptide was commercially available.

The synthesis of the third key dipeptide KD-3c, Fmoc-Glu-(OtBu)-Leu-OtBu was performed by coupling of commercially available 1-butyl Leucinate.HCl with Fmoc-Glu-(OtBu) in DCM at high dilution in the presence of EDAC, HCl, HOBt and DIPEA.

Synthesis of Foxy-5 by Route C from the three dipeptide fragments KD-1c, KD-2c and KD-3c is finally initiated by coupling of protected key dipeptides KD-3c, Fmoc-Glu-(OtBu)-Leu-OtBu with KD-2c, Fmoc-Gly-Cys(Trt)-OH to afford tetrapeptide Fmoc-Gly-Cys(Trt)-Glu(OtBu)-Leu-OtBu (SEQ_ID NO 6), which is subsequently reacted with KD-1c, Fmoc-Met-Asp(OtBu)-OH to afford protected hexapeptide Fmoc-Met-Asp(OtBu)-Gly-Cys(Trt)-Glu(OtBu)-Leu-OtBu (SEQ_ID NO 4) which was subsequently subjected to Fmoc deprotection with DBU in DCM followed by coupling with formic acid in the presence of EDC·HCl, HOBt·H$_2$O and DIPEA to yield For-Met-Asp(OtBu)-Gly-Cys(Trt)-Glu(OtBu)-Leu-OtBu (SEQ_ID NO 15).

This protected hexapeptide (SEQ_ID NO 15) was globally deprotected (Trt and tBu groups) by dissolution and stirring in a cocktail of TFA/(i-Pr)₃SiH/DTT. After completion of reaction, the crude product was obtained as a solid in 97% yield (9.5 gr) by precipitation with THF/MTBE. Chromatographic purification afforded the desired hexapeptide For-Met-Asp-Gly-Cys-Glu-Leu-OH (Foxy-5) in 97.6% purity.

Figure 7:
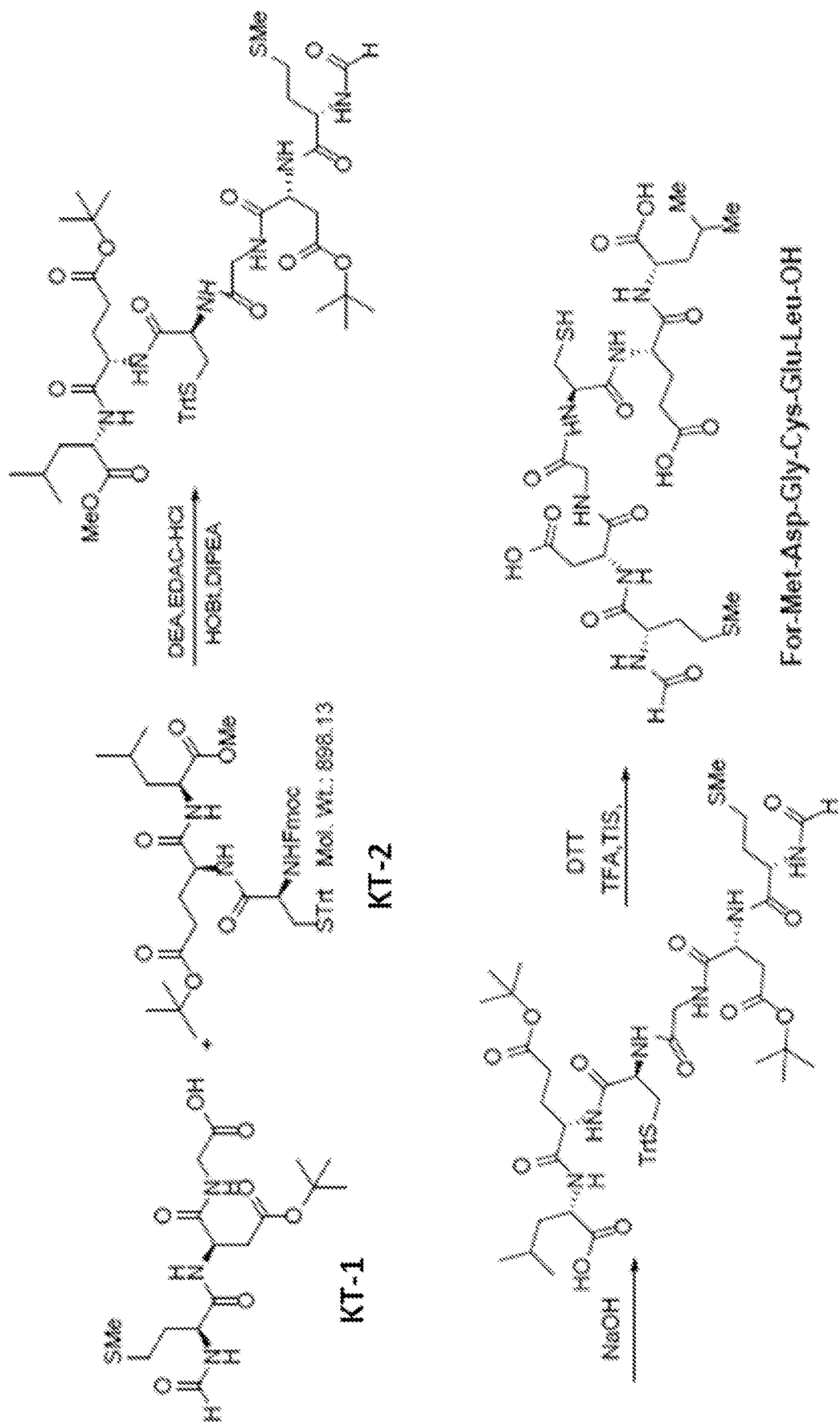
FIG. 7 illustrates a 3+3 strategy for the formation of Foxy-5 based on coupling Key Tripeptide 1 (KT-1) with Key Tripeptide 2 (KT-2) followed by [1] saponification of the leucine methyl ester and [2] deprotection of tert-butyl and trityl protecting groups.
Figure 7A:
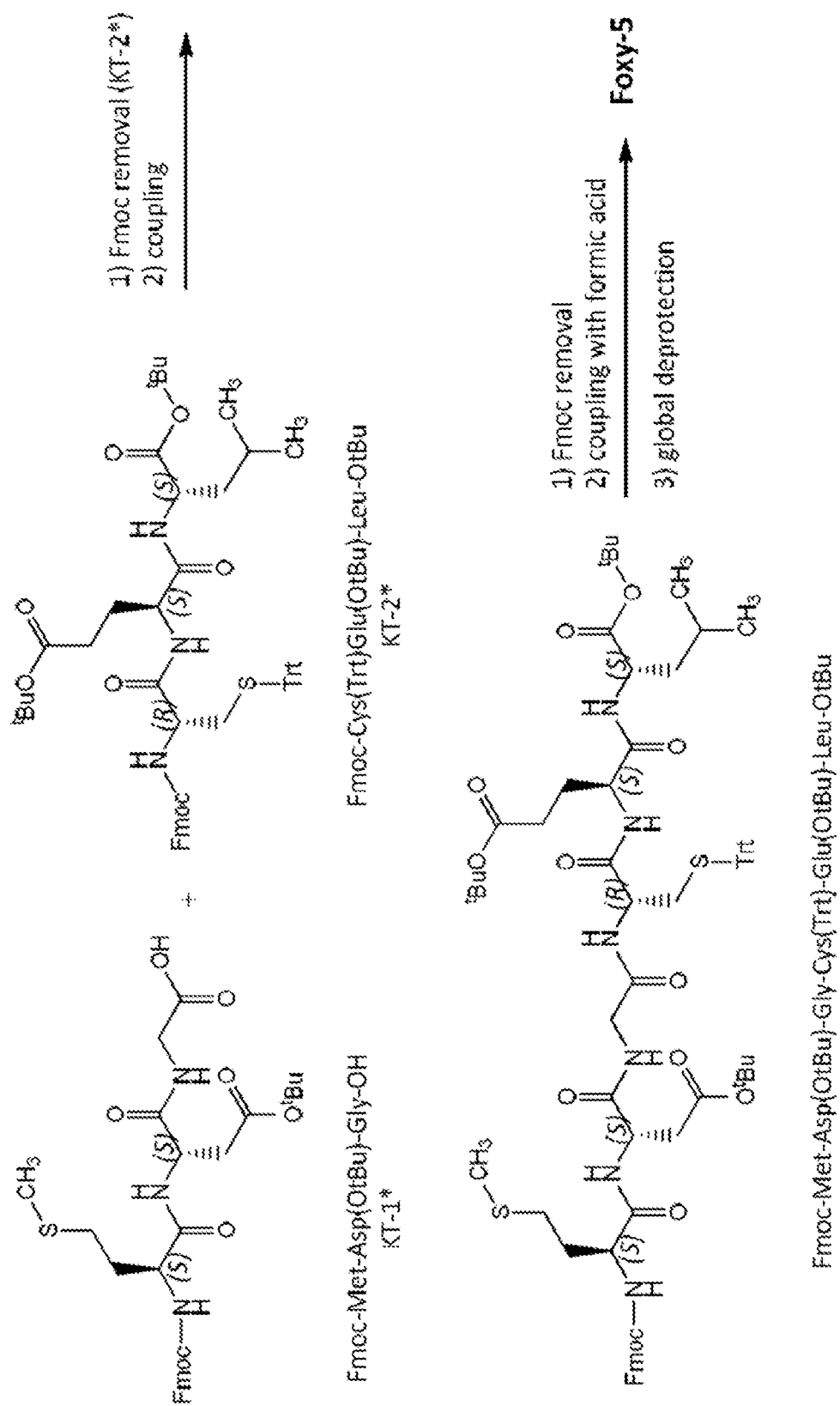
FIG. 7a illustrates a 3+3 strategy for the formation of Foxy-5 based on coupling Key Tripeptide 1* (KT-1*) with Key Tripeptide 2* (KT-2*) followed by Fmoc deprotection with DBU, coupling with formic acid and deprotection of tert-butyl and trityl protecting groups to afford the desired Foxy-5.

3+3 Coupling Strategy (FIGS. 7 and 7a)

Synthesis of fragment KT-1 (For-Met-Asp(OtBu)-Gly-OH) is initiated by conversion of glycine to glycine methyl ester. Coupling hereof with the commercially available Fmoc-Asp-(O-tBu) gives Fmoc-Asp(OtBu)-Gly-OMe. Fmoc deprotection followed by coupling with the commercially available For-Met-OH gives For-Met-Asp(OtBu)-Gly-OMe. The latter upon hydrolysis of the methyl ester furnishes the desired fragment KT-1.

To allow for an optional later introduction of the formyl group (or another acyl group), a modified version of fragment KT-1, KT-1* (Fmoc-Met-Asp(OtBu)-Gly-OH) is produced as well, wherein dipeptide Fmoc-Asp(OtBu)-Gly-OMe is first Fmoc deprotected, followed by coupling with commercially available Fmoc-Met-OH.

Synthesis of Fragment KT-2 (Fmoc-Cys(Trt)Glu(OtBu)-Leu-OMe) is initiated by conversion of L-Leucine to its methyl ester. Amide bond formation hereof with commercially available Fmoc-Glu-(OtBu) gives Fmoc-Glu(OtBu)-Leu-OMe. Deprotection and further coupling with commercially available Fmoc-Cys(Trt)-OH furnishes the desired fragment KT-2.

Synthesis of alternative fragment KT-2* (Fmoc-Cys(Trt) Glu(OtBu)-Leu-OtBu) is realized by coupling of t-butyl Leucinate.HCl with Fmoc-Glu-(OtBu) to produce Fmoc-Glu-(OtBu)-Leu-OtBu (i.e. KD-3c). The dipeptide is not isolated but coupled directly (after Fmoc deprotection with DBU) with Fmoc-Cys(Trt)-OH to produce the desired fragment KT-2*.

Synthesis of Foxy-5 from the tripeptide fragments KT-1 and KT-2 is realized beginning with the Fmoc-deprotection of KT-2. Subsequent coupling with KT-1 affords For-Met-Asp(OtBu)-Gly-Cys(Trt)-Glu(OtBu)-Leu-OMe. Saponification hereof under basic conditions yields For-Met-Asp (OtBu)-Gly-Cys(Trt)-Glu(OtBu)-Leu-OH, and the latter upon deprotection of tert-butyl and trityl protecting groups gives the desired hexapeptide Foxy-5 in crude form.

Alternatively (FIG. 7a), synthesis of Foxy-5 from the tripeptide fragments KT-1* and KT-2* is realized beginning with the Fmoc-deprotection of KT-2*. Subsequent coupling with KT-1* affords Fmoc-Met-Asp(OtBu)-Gly-Cys(Trt)-Glu(OtBu)-Leu-OtBu (SEQ_ID NO 4), which is subsequently subjected to Fmoc deprotection with DBU followed by coupling with formic acid to yield For-Met-Asp(OtBu)-Gly-Cys(Trt)-Glu(OtBu)-Leu-OtBu For-Met-Asp-Gly-Cys-Glu-Leu-OH This protected hexapeptide is globally deprotected (Trt and tBu groups) to afford Foxy-5 in crude form. Chromatographic purification afforded the desired hexapeptide For-Met-Asp-Gly-Cys-Glu-Leu-OH (Foxy-5) in 97.6% purity.

4+1+1 Coupling Strategy

Synthesis of Foxy-5 by the 4+1+1 coupling strategy is initiated by sequential coupling of tetrapeptide Fmoc-Gly-Cys(Trt)-Glu(OtBu)-Leu-OtBu (SEQ_ID NO 6) with Fmoc-Asp-OtBu and Fmoc-Met followed by Fmoc removal, formylation and deprotection. The tetrapeptide itself is provided by coupling of dipeptide fragments KD-3c Fmoc-Glu-(OtBu)-Leu-OtBu and KD-2c Fmoc-Gly-Cys(Trt)-OH described hereinabove.

The tetrapeptide Fmoc-Gly-Cys(Trt)-Glu(OtBu)-Leu-OtBu (SEQ_ID NO 6) is subsequently coupled with Fmoc-Asp-OtBu to afford protected pentapeptide Fmoc-Asp (OtBu)-Gly-Cys(Trt)Glu(OtBu)-Leu-OtBu (SEQ_ID NO 10) followed by coupling with Fmoc-methionine to afford the protected hexapeptide Fmoc-Met-Asp(OtBu)-Gly-Cys (Trt)Glu(OtBu)-Leu-OtBu (SEQ_ID NO 4). This is subsequently subjected to Fmoc deprotection with DBU followed by coupling with formic acid to yield For-Met-Asp(OtBu)-Gly-Cys(Trt)-Glu(OtBu)-Leu-OtBu (SEQ_ID NO 15). This protected hexapeptide is globally deprotected (Trt and tBu groups) to afford Foxy-5 in crude form. Chromatographic purification afforded the desired hexapeptide For-Met-Asp-Gly-Cys-Glu-Leu-OH (Foxy-5) in 97.6% purity.

Figure 8:
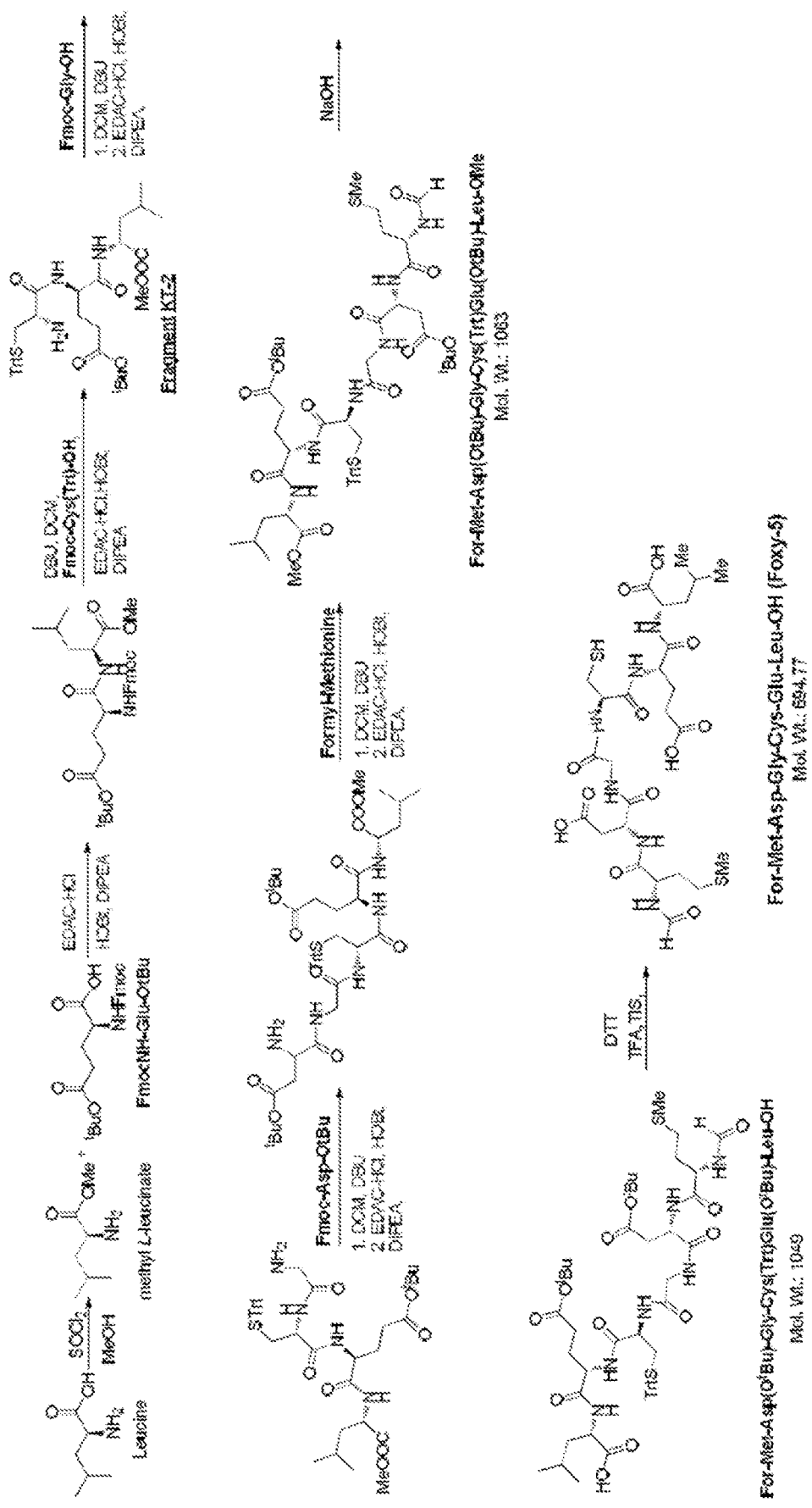
FIG. 8 illustrates a 3+1+1+1 strategy for the formation of Foxy-5 based on sequential elongation of Key Tripeptide 2 (KT-2) with amino acids Gly, Asp and formyl-Met.
Figure 8A:
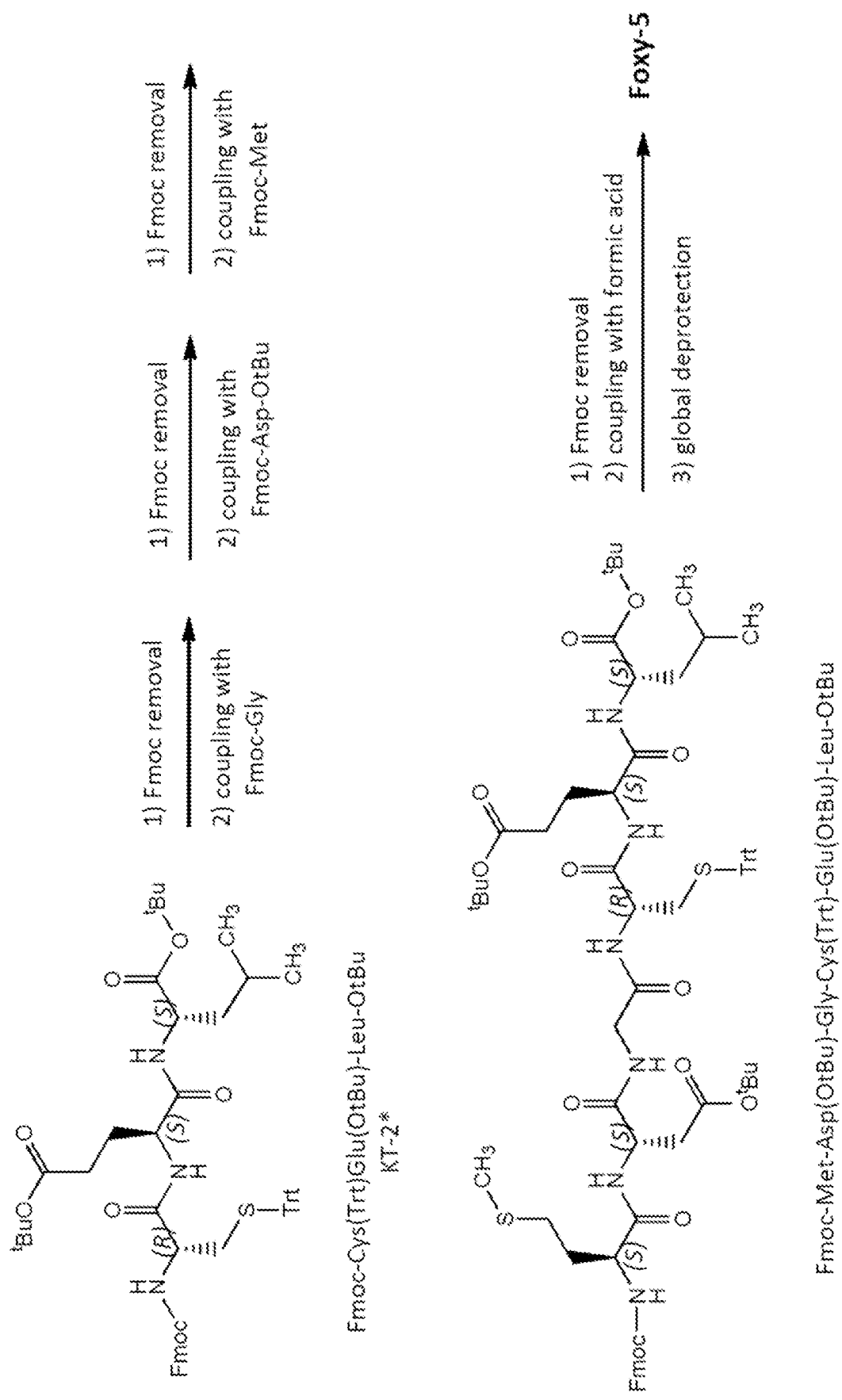
FIG. 8a illustrates a 3+1+1+1 strategy for the formation of Foxy-5 based on sequential elongation of Key Tripeptide 2* (KT-2*) with amino acids Fmoc-Gly, Fmoc-Asp-OtBu and Fmoc-Met. The resulting hexapeptide is subjected to Fmoc deprotection with DBU, coupling with formic acid and deprotection of tert-butyl and trityl protecting groups to afford the desired Foxy-5.

3+1+1+1 Coupling Strategy (FIGS. 8 and 8a)

Synthesis of Foxy-5 by the 3+1+1+1 coupling strategy is initiated by sequential coupling of fragment KT-2 (Fmoc-Cys(Trt)Glu(OtBu)-Leu-OMe) with Fmoc-Gly-OH to afford protected tetrapeptide Fmoc-Gly-Cys(Trt)Glu(OtBu)-Leu-OMe (SEQ_ID NO SEQ_ID NO 7) followed by coupling with Fmoc-Asp-OtBu to afford protected pentapeptide Fmoc-Asp(OtBu)-Gly-Cys(Trt)Glu(OtBu)-Leu-OMe (SEQ_ID NO 9) followed by coupling with formyl-methionine to afford Foxy-5 in protected form, i.e. For-Met-Asp(OtBu)-Gly-Cys(Trt)Glu(OtBu)-Leu-OMe (SEQ_ID NO 3).

Synthesis of Foxy-5 itself is finally achieved by the same strategy as for the 3+3 coupling strategy hereinabove, i.e. by by saponification of the leucine methyl ester to afford For-Met-Asp(OtBu)-Gly-Cys(Trt)Glu(OtBu)-Leu-OH (SEQ_ID NO 4), and final removal herefrom of the trityl and tert-butyl protection groups to afford Foxy-5 in crude form.

Alternatively, Synthesis of Foxy-5 by the 3+1+1+1 coupling strategy is initiated by sequential coupling of fragment KT-2* (Fmoc-Cys(Trt)Glu(OtBu)-Leu-OtBu) with Fmoc-Gly-OH to afford protected tetrapeptide Fmoc-Gly-Cys(Trt) Glu(OtBu)-Leu-OtBu (SEQ_ID NO 6) followed by coupling with Fmoc-Asp-OtBu to afford protected pentapeptide Fmoc-Asp(OtBu)-Gly-Cys(Trt)Glu(OtBu)-Leu-OtBu (SEQ_ID NO 10) followed by coupling with Fmoc-methionine to afford the protected hexapeptide Fmoc-Met-Asp(OtBu)-Gly-Cys(Trt)Glu(OtBu)-Leu-OtBu (SEQ_ID NO 4). This is subsequently subjected to Fmoc deprotection with DBU followed by coupling with formic acid to yield For-Met-Asp(OtBu)-Gly-Cys(Trt)-Glu(OtBu)-Leu-OtBu (SEQ_ID NO 15). This protected hexapeptide is globally deprotected (Trt and tBu groups) to afford Foxy-5 in crude form. Chromatographic purification afforded the desired hexapeptide For-Met-Asp-Gly-Cys-Glu-Leu-OH (Foxy-5) in 97.6% purity.

It is noted that the tripeptide For-Met-Asp-Gly-OH and the protected derivatives described herein, For-Met-Asp (OtBu)-Gly-OMe and For-Met-Asp(OtBu)-Gly-OH are novel compounds. Likewise, the tripeptide Met-Asp-Gly and the protected derivatives described herein, Fmoc-Met-Asp(OtBu)-Gly-OMe, Fmoc-Met-Asp(OtBu)-Gly-OtBu and Fmoc-Met-Asp(OtBu)-Gly-OH (KT-1*) are novel compounds. Likewise, the tripeptide Cys-Glu-Leu-OH and the protected derivatives described herein, Fmoc-Cys(Trt)Glu (OtBu)-Leu-OMe, (Fmoc-Cys(Trt)Glu(OtBu)-Leu-OtBu) and Cys-Glu-Leu-OMe are novel compounds.

It is further noted that tetrapeptides Fmoc-Gly-Cys(Trt) Glu(OtBu)-Leu-OMe (SEQ_ID NO 7) and Fmoc-Gly-Cys (Trt)Glu(OtBu)-Leu-OtBu (SEQ_ID NO 6), the protected pentapeptides Fmoc-Asp(OtBu)-Gly-Cys(Trt)Glu(OtBu)-Leu-OMe (SEQ_ID NO 9) and Fmoc-Asp(OtBu)-Gly-Cys (Trt)Glu(OtBu)-Leu-OtBu (SEQ_ID NO 10), and the protected Foxy-5 derivatives For-Met-Asp(OtBu)-Gly-Cys(Trt)

Glu(OtBu)-Leu-OMe (SEQ_ID NO 3) and For-Met-Asp(OtBu)-Gly-Cys(Trt)Glu(OtBu)-Leu-OtBu (SEQ_ID NO 15) are all novel compounds.

In another aspect of the invention there is thus provided a protected tripeptide fragment of Foxy-5 (For-Met-Asp-Gly-Cys-Glu-Leu-OH) selected from:
a) $PG_1$-Cys($PG_2$)Glu($OPG_3$)-Leu-$OR_1$
b) $PG_5$-Met-Asp($OPG_4$)-Gly-$OR_2$
c) $PG_1$-Gly-Cys($PG_2$)Glu($OPG_3$)-Leu-$OR_1$ wherein $PG_1$ is selected from H and protecting groups such as fluorenylmethyloxycarbonyl (Fmoc) or Boc, $PG_2$ is selected from H and protecting groups selected from acetonide (pseudoproline, $\psi^{Me,Me}Pro$), trityl (Trt), $PG_3$ is selected from H and protecting groups selected from tert-butyl (tBu), $PG_5$ is formyl or a base-sensitive protecting group such as fluorenylmethyloxycarbonyl (Fmoc), $PG_4$ is selected from H and protecting groups selected from tert-butyl (tBu), and $R_1$ and $R_2$ are independently chosen from H and $C_1$-$C_6$ alkyl, such as methyl, ethyl or tert-butyl (tBu).

In a preferred embodiment there is provided a protected tripeptide fragment of Foxy-5 which is $PG_1$-Cys($PG_2$)Glu($OPG_3$)-Leu-$OR_1$, wherein $PG_1$, $PG_2$, $PG_3$ and $R_1$ are as defined above. In a particularly preferred embodiment said tripeptide fragment is Fmoc-Cys(Trt)Glu(OtBu)-Leu-OMe.

In another preferred embodiment there is provided a protected tripeptide fragment of Foxy-5 which is $PG_5$-Met-Asp($OPG_4$)-Gly-$OR_2$, wherein $PG_5$, $PG_4$ and $R_2$ are as defined above. In a particularly preferred embodiment said tripeptide fragment is Fmoc-Met-Asp(OtBu)-Gly-OtBu.

In a further aspect of the invention, there is provided a solution phase method for preparing a protected derivative of Foxy-5, $PG_5$-Met-Asp(OtBu)-Gly-Cys(Trt)-Glu(OtBu)-Leu-OtBu, the method comprising:
a. Coupling dipeptides Fmoc-Glu-(OtBu)-Leu-OtBu (KD-3c) with Fmoc-Gly-Cys(Trt)-OH (KD-2c) to afford tetrapeptide Fmoc-Gly-Cys(Trt)-Glu(OtBu)-Leu-OtBu (SEQ_ID NO 6), followed by coupling with $PG_5$-Met-Asp(OtBu)-OH, or
b. Coupling tripeptide $PG_5$-Met-Asp(OtBu)-Gly-OH with Fmoc-Cys(Trt)-Glu(OtBu)-Leu-OtBu (KT-2*), or
c. Sequentially coupling tripeptide Fmoc-Cys(Trt)Glu(OtBu)-Leu-OtBu (KT-2*) with Fmoc-Gly-OH, Fmoc-Asp-OtBu and $PG_5$-Met, or
d. Sequentially coupling tetrapeptide Fmoc-Gly-Cys(Trt)-Glu(OtBu)-Leu-OtBu (SEQ_ID NO 6) with Fmoc-Asp-OtBu and $PG_5$-Met, optionally followed by purification of the crude hexapeptide by column chromatography followed by precipitation as a solid from an organic solvent, and wherein $PG_5$ is formyl or a base sensitive protecting group such as Fmoc.

The present invention in a further aspect provides a solution phase method for converting $PG_5$-Met-Asp(OtBu)-Gly-Cys(Trt)-Glu(OtBu)-Leu-OtBu to Foxy-5 (For-Met-Asp-Gly-Cys-Glu-Leu-OH), the method comprising either:
for $PG_5$=formyl:
i. Deprotection of For-Met-Asp(OtBu)-Gly-Cys(Trt)-Glu(OtBu)-Leu-OtBu (SEQ_NO 15) to afford Foxy-5 in crude form,
or for $PG_5$=a base sensitive protecting group such as Fmoc:
ii. Removal of $PG_5$ from hexapeptide $PG_6$-Met-Asp(OtBu)-Gly-Cys(Trt)-Glu(OtBu)-Leu-OtBu followed by coupling with formic acid to yield For-Met-Asp(OtBu)-Gly-Cys(Trt)-Glu(OtBu)-Leu-OtBu (SEQ_NO 15),
iii. Deprotection of For-Met-Asp(OtBu)-Gly-Cys(Trt)-Glu(OtBu)-Leu-OtBu (SEQ_NO 15) to afford Foxy-5 in crude form,
followed by:
a. Optional purification of the crude product by column chromatography, optionally followed by precipitation as a solid from an organic solvent,
b. Optional precipitation of the formed Foxy-5 hexapeptide as an alkaline or acidic salt in solid form, such as in crystalline form.

In a preferred embodiment, $PG_5$ is Fmoc.

EXPERIMENTAL

2+2+2 Routes

Example 1—Preparation of Key Dipeptide KD-1a
Boc-Met-Asp(OtBu)-OH

The synthesis of the methyl ester Boc-Met-Asp(OtBu)-OMe of the target dipeptide was performed as follows: Boc-Met-OH (2.6 g, 10.4 mmol, 1.0 eq) was dissolved in DMF (dry) (25 ml), DCC (2.2 g, 10.4 mmol, 1.0 eq), and HOAt (1.4 g, 10.4 mmol, 1.0 eq) were added. In a dry 100 ml round-bottom flask H-Asp(OtBu)-OMe·HCl (2.5 g, 10.4 mmol, 1.0 eq) was combined with DIPEA (1.8 ml, 10.4 mmol, 1.0 eq) in DMF (dry) (50 ml). Both solutions were cooled to 0° C. After 10 min, the solution containing the aspartate derivative was transferred drop-wise to the methionine solution. The reaction was allowed to warm to room temperature over 72 h. After an aqueous acid (0.5 M citric acid) and base (sat. $NaHCO_3$) work-up, the obtained material was analyzed by LCMS. Although some solvent signals (EtOAc) and impurities were observed, the signals were in agreement with the structure of compound Boc-Met-Asp(OtBu)-OMe.

In the subsequent step, the intermediate methyl ester Boc-Met-Asp(OtBu)-OMe (3.5 g, 8.1 mmol, 1.0 eq) was dissolved in 1,4-dioxane/MeOH (14:1) (75 ml) and a freshly prepared 3.6 M NaOH (aq) solution, (2.3 ml, 8.5 mmol, 1.0 eq) was added. The reaction was allowed to stir at room temperature for 18 h and the reaction mixture was sampled. LCMS analysis indicated that the starting material was completely consumed. The main signal at 2.031 minutes (70 area %) showed the target molecule Boc-Met-Asp(OtBu)-OH mass (M=420 g/mol, found: m/z+=421 $[M+H]^+$, 443 $[M+Na]^+$). A side-product was observed that could be identified as Boc-Met-Asp-OH; and therefore shorter reaction times (<18 h) for the saponification reaction are recommended. The target compound, Key Dipeptide KD-1a (Boc-Met-Asp(OtBu)-OH) was obtained in 63% yield, 70 area % (LCMS) pure.

Example 2—Preparation of Key Dipeptide KD-2a
Cbz-Gly-Cys($\psi^{Me,Me}Pro$)-OH

To a 250 ml round bottom flask were added L-cysteine hydrochloride monohydrate (5.0 g, 28.5 mmol) and acetone (80 ml, 1088 mmol) (p.a. quality). The reaction (0.36 molar) was then heated to reflux for 1.5 h. After 30 minutes, the white suspension turned into thick slurry. Filtration and subsequent removal of the excess of acetone yielded a white amorphous solid 4.7 g. $^1H$ NMR analysis indicated that approximately 50% of the unreacted cysteine remained. In order to improve the yield and quality of the proline acetonide, the white amorphous solid (4.72 g) was treated a second time with acetone (200 ml) in a more dilute reaction mixture (0.14 M). The suspension was refluxed for 2 h. The suspension was then slowly cooled to room temperature and then 30 minutes at 0° C. The ice cold suspension was filtered through a p3 glass filter and rinsed with acetone (2×10 ml). Residual acetone was removed in vacuo. The desired acetonide H-Cys($\psi^{Me,Me}$Pro)-OH (4.4 g, 27 mmol, 95% yield) was obtained in excellent yield and purity as a white powder. The $^1$H NMR (DMSO) spectrum of the product was in agreement with the target molecule structure and did not show signals of the starting material H-Cys-OH.

In the subsequent step, the acetonide intermediate H-Cys($\psi^{Me,Me}$Pro)-OH (1.0 g, 6.2 mmol, 1.0 eq) was dissolved in DMF (50 ml) and triethylamine (2.6 ml, 19 mmol, 3.0 eq) was added. After stirring for 10 minutes at room temperature, commercially available Cbz-Gly-OSu (2.4 g, 6.2 mmol, 1.0 eq) was added and the reaction mixture was allowed to stir for 18 h during which period the mixture remained a suspension.

The reaction mixture was acidified by addition of 4 M hydrochloric acid in 1,4-dioxane (10.11 ml, 10.11 mmol) until pH=4. At this point a solid precipitated; which was collected by filtration. The residue mainly consisted of Et3N·HCl salt. 250 ml water was added to the filtrate and it was extracted with EtOAc (3×50 ml). The combined organic phase was then washed with brine (2×50 ml), dried over Na2SO4, filtered and concentrated to afford an off-white solid (1.58 g). LCMS analysis of the combined organic phase showed the main signal at 2.003 minutes (77 area %) representing the dipeptide Cbz-Gly-Cys($\psi^{Me,Me}$Pro)-OH (M=352 g/mol, found: m/z-=351 [M−H]−, 703 [2M−H]−). At 1.779 minutes (9 area %), the Cbz-Gly-OH was observed (the succinimide ester Cbz-Gly-OSu at 1.887 minutes was not observed, indicating hydrolysis of the starting material).

The aqueous phase was then further acidified to pH=1 and extracted again with EtOAc (3×50 ml). The combined organic phase was washed with brine (3×50 ml), dried over Na2SO4, filtered, and concentrated to afford a yellowish oil (2.60 g). LCMS analysis showed the target molecule at 2.006 min (66 area %). The main side-product signal was observed at 1.778 minutes (20 area %), and was attributed to Cbz-Gly-OH. The combined yield, without further purification, of dipeptide Cbz-Gly-Cys($\psi^{Me,Me}$Pro)-OH was 4.2 g (83%, based on 70% LCMS purity). The main impurity was identified as Cbz-Gly-OH.

Example 2a Preparation of Alternative Dipeptide KD-1c Fmoc-Met-Asp(OtBu)-OH

Fmoc-Met-Asp(OtBu)-OH Fmoc-Met-OSu was prepared according to WO1990008773A1, in situ, by the reaction of Fmoc-Met-OH (14.87 g), N-Hydroxysuccinimide (HOSu, 5.52 g), and dicyclohexyl carbodiimide (DCC, 8.26 g) in tetrahydrofuran (THF, 200 ml) at 0° C. for 3.5 hrs. Precipitated dicyclohexylurea (DCU) was removed by filtration and the THF filtrate was added to a cold solution of H-Asp(OtBu)-OH in 220 ml of 10:1 water/THF to which had been added 40 ml of N sodium hydroxide. After stirring the reaction mixture at room temperature overnight, solid citric acid (20 g) was added along with EtOAc (600 ml). The EtOAc layer was separated, washed with 10% citric acid and brine, and dried (magnesium sulphate). Evapo-ration of the EtOAc solution gave a residue which was dissolved in 200 ml of EtOAc and treated with dicyclohexylamine (DCHA, 7.84 ml) to precipitate 17.93 g of the DCHA salt of the desired product, mp 159-162° C.

Example 3—Preparation of Key Dipeptide KD-3a H-Glu(OBn)-Leu-OBn

In a 250 ml round bottom flask, a cooled solution of commercially available Cbz-Glu(OtBu)-OH (5.0 g, 14.8 mmol, 1.0 eq) was combined with HOAt (2.4 g, 17.8 mmol, 1.2 eq), and DCC (3.7 g, 17.8 mmol, 1.2 eq) in anhydrous MeCN (25 ml). To this solution was added a mixture of H-Leu-OtBu·HCl (3.3 g, 14.8 mmol, 1.0 eq) and DIPEA (2.58 ml, 14.82 mmol) in anhydrous MeCN (50 ml). The resulting reaction mixture (0.2 molar) was stirred at 0° C. with a gradual increase to room temperature in 18 h. The reaction mixture was then concentrated in vacuo to afford 9.1 g (max. 83% yield, based on HPLC purity of 70 area %) of a thick yellow oil that solidified slowly upon standing for several hours. A part (5.2 g) hereof was suspended in 50 ml EtOAc and 30 ml H2O was added. The organic phase was washed and evaporated; this afforded 2.9 g of a white solid. HPLC analysis showed the product at 4.105 minutes (76 area %). 1H NMR analysis was in agreement with the target molecule, and Cbz-Glu(OtBu)-Leu-OtBu was obtained in a calculated yield of 52% and in average purity of 76% (based on HPLC analysis) without chromatography and 63% yield with 95% purity based on $^1$H NMR analysis. The material was used in the subsequent reactions without further purification.

Finally, following a thorough catalyst screening, Noblyst Pd/C catalyst type P1141 was then used to perform the Cbz deprotection to furnish the target dipeptide KD-3a, H-Glu(OBn)-Leu-OBn. For this reaction, Cbz-Glu(OtBu)-Leu-OtBu (1.5 g, 3.0 mmol, 1.0 eq) was dissolved in MeOH (20 ml) and Pd (10% on activated carbon, type Noblyst P1141) (500 mg, 470 μmol, 0.2 eq) was added. H$_2$ was bubbled through the solution for 1 h. The reaction was then allowed to stir under a hydrogen atmosphere (1 atm.) for 18 h. HPLC analysis (taken after 18 h) showed full conversion of the starting material and showed mainly the toluene signal at 3.391 minutes and the target molecule signal at 2.843 minutes. The reaction mixture was filtered through celite in a P3 glass filter. The residue was rinsed with MeOH (3×1 ml) and the filtrate was concentrated in vacuo. The target compound HGlu(OtBu)-Leu-OtBu was obtained as yellowish oil, 1.02 g (92% yield) and 95 area % purity, based on HPLC analysis. This material was used for subsequent reactions as it was obtained.

Example 3a—Preparation of Alternative Key Dipeptide KD-3c Fmoc-Glu-(OtBu)-Leu-OtBu 50 gr 1-butyl Leucinate.HCl was coupled with 1.3 eq Fmoc-Glu-(OtBu) in dichloromethane at high dilution (50 vol) in the presence of EDAC, HCl (2.0 eq), and HOBt (2.0 eq) and DIPEA (5.0 eq) at initially 0-5° C. for 1 hr followed by 15-20° C. for 1 hr, which afforded dipeptide Fmoc-Glu-(OtBu)-Leu-OtBu (KD-3c). Identity was confirmed by $^1$H NMR and mass spectometry. For reaction with Fmoc-Gly-Cys(Trt)-OH, product isolation was omitted and the dichloromethane solution used directly in Example 4a after aqueous workup.

Example 4—Preparation of Tetrapeptide Gly-Cys ($\psi^{Me,Me}$Pro)-Glu(OtBu)-Leu-OtBu (SEQ ID NO 5)

The subsequent reaction involved the coupling of the dipeptides H-Glu(OtBu)-Leu-OtBu and Cbz-Gly-Cys($\psi^{Me,Me}$Pro)-OH in the presence of DCC and HOAt.

The coupling reaction was performed as follows: H-Glu(OtBu)-Leu-OtBu (898 mg, 2.4 mmol, 1.0 eq) was dissolved in dry DMF (20 ml) and the solution was cooled to 0° C. Then, DCC (498 mg, 2.4 mmol, 1.0 eq) and HOAt (328 mg, 2.4 mmol, 1.0 eq) were added. To the mixture was added Cbz-Gly-Cys($\psi^{Me,Me}$Pro)-OH (850 mg, 2.4 mmol, 1.0 eq) and the reaction mixture was stirred, allowing it to gradually warm to room temperature for 18 h.

The reaction mixture was filtered through celite in a P3 glass filter. The residue was rinsed with DMF (2×5 ml). To the filtrate was added 100 ml H$_2$O upon which a milky, colloidal-like solution formed. EtOAc (50 ml) was added. The phase separation was very slow and it was decided to add approx. 20 gr of NaCl to the mixture upon which the mixture cleared up slightly and a clear phase separation appeared. The aqueous phase was then extracted twice with EtOAc (50 ml). The resulting aqueous phase was sampled for LCMS analysis and did not contain the product mass. The combined organic phases was worked-up according to the standard procedure, which yielded 1.41 g of a yellowish oil that solidified when co-evaporated with Et2O to an off-white voluminous solid (1.41 g, 58% yield, based on 70% purity). LCMS analysis indicated that approximately 6 area % DCC was present, corresponding to the signal at 2.034 minutes (M=224 g/mol, found: m/z+=225 [M+H]', 449 [M+Na]'). At 2.297 minutes, an unknown compound was observed with m/z+=452, 579 (16 area %). The target molecule Cbz-Gly-Cys($\psi^{Me,Me}$Pro)-Glu(OtBu)-Leu-OtBu was observed at 2.404 minutes (76 area %) (M=706 g/mol, found: m/z+=707 [M+H]', 729 [M+Na]').

The subsequent Cbz-deprotection of Cbz-Gly-Cys($\psi^{Me,Me}$Pro)-Glu(OtBu)-Leu-OtBu was then performed with the Noblyst P1141 catalyst that was previously mentioned in the deprotection reaction of dipeptide Cbz-Glu(OtBu)-Leu-OtBu. In that particular case, this catalyst was selected because it showed good reactivity in a screening experiment and the starting material was fully converted within 18 hours reaction time. Therefore, these conditions were also applied for the selective Cbz-deprotection of the tetrapeptide Cbz-Gly-Cys($\psi^{Me,Me}$Pro)-Glu(OtBu)-Leu-OtBu. An initial test reaction indicated that the hydrogenation of the tetrapeptide (Cbz-Gly-Cys($\psi^{Me,Me}$Pro)-Glu(OtBu)-Leu-OtBu) required more Pd/C than was used for the dipeptide Cbz-Glu(OtBu)-Leu-OtBu for a satisfactory reaction rate. For this reaction, Cbz-Gly-Cys($\psi^{Me,Me}$Pro)-Glu(OtBu)-Leu-OtBu (700 mg, 1.0 mmol, 1.0 eq) was dissolved in MeOH (10 ml) and Pd/C (Noblyst P1141, 10% (w/w) Pd, 60% H$_2$O) (700 mg, 40 μmol, 4 mol %) was added. The reaction mixture was allowed to stir under a hydrogen atmosphere (1 atm.). The reaction was followed by HPLC analysis.

After 5 h reaction time, still 23 area % of the starting material was observed. After 24 h, HPLC analysis indicated that 12 area % of the starting material was still left. Then, an additional amount of the Pd/C cat. (200 mg) was added. After 72 hours total reaction time, HPLC analysis showed that the starting material had almost completely been consumed (0.84 area % left). The reaction mixture was filtered through hyflo in a P3 glass filter and rinsed with MeOH (3×5 ml). The filtrate was concentrated in vacuo to afford 550 mg of yellowish oil. HPLC analysis showed the main signal at 1.929 min (81 area %) that displayed the target molecule mass (M=572 g/mol, found: m/z+573 [M+H]+).

Tetrapeptide H-Gly-Cys($\psi^{Me,Me}$Pro)-Glu(OtBu)-Leu-OtBu (550 mg, 0.78 mmol, 79% yield) was obtained in 80% purity (based on LCMS).

Example 4a—Preparation of Alternative Tetrapeptide Fmoc-Gly-Cys(Trt)-Glu(OtBu)-Leu-OtBu (SEQ ID NO 6)

The subsequent reaction of obtained dipeptide KD-3c Fmoc-Glu-(OtBu)-Leu-OtBu is performed using the dichloromethane solution referred to above (Example 3a). Fmoc deprotection was achieved with DBU and coupling with 1.3 eq Fmoc-Gly-Cys(Trt)-OH (commercially available) is performed in the presence of DIPEA (3 eq), EDC·HCl (2.0 eq) and HOBt (2.0 eq) to afford protected tetrapeptide Fmoc-Gly-Cys(Trt)-Glu(OtBu)-Leu-OtBu (SEQ_ID NO 6). The DCM layer is washed with water and brine, concentrated to 10-15 vol and used as such in the next stage (example 5a) without isolation.

Example 5—Preparation of hexapeptide Boc-Met-Asp(OtBu)-Gly-Cys($\psi^{Me,Me}$Pro)-Glu(OtBu)-Leu-OtBu (SEQ ID NO 2)

The peptide coupling of Boc-Met-Asp(OtBu)-OH and H-Gly-Cys($\psi^{Me,Me}$Pro)-Glu(OtBu)-Leu-OtBu to afford hexapeptide Boc-Met-Asp(OtBu)-Gly-Cys($\psi^{Me,Me}$Pro)-Glu(OtBu)-Leu-OtBu was then performed in presence of coupling reagent DCC and additive HOAt in DMF at room temperature for 18 h.

For this reaction, Boc-Met-Asp(OtBu)-OH (200 mg, 0.48 mmol, 1.0 eq), was dissolved in DMF (2.0 ml) and cooled in an ice bath. To the clear solution were added HOAt (65 mg, 0.48 mmol, 1.0 eq), and DCC (98 mg, 0.48 mmol, 1.0 eq). After 15 minutes, HCys($\psi^{Me,Me}$Pro)-Glu(OtBu)-Leu-OtBu (272 mg, 0.48 mmol, 1.0 eq) was added and the reaction mixture was stirred for 18 h while slowly warming to room temperature. The reaction mixture was then worked-up according to standard procedure. LCMS analysis of the worked-up batch showed the target molecule Boc-Met-Asp(OtBu)-Gly-Cys($\psi^{Me,Me}$Pro)-Glu(OtBu)-Leu-OtBu at 2.760 minutes retention time (M=974 g/mol, found: m/z+=975 [M+H]', 997 [M+Na]'). The target molecule Boc-Met-Asp(OtBu)-Gly-Cys($\psi^{Me,Me}$Pro)-Glu(OtBu)-Leu-OtBu was obtained in 76% yield (420 mg, 0.36 mmol) based on a purity of 84% (LCMS) as a voluminous white solid.

Example 5a Preparation of Alternative Hexapeptide Fmoc-Met-Asp(OtBu)-Gly-Cys(Trt)-Glu(OtBu)-Leu-OtBu (SEQ_ID NO 4) and Conversion Hereof to Foxy-5

Fmoc-Gly-Cys(Trt)-Glu(OtBu)-Leu-OtBu (SEQ_ID NO 6) as obtained hereinabove in Example 4a as a concentrated DCM solution is first reacted with DBU to achieve Fmoc deprotection. Before proceeding with the next coupling step, the reaction mass is passed through a silica plug to remove DBU. After silica plug treatment the DCM solution is reacted (after liberation) with Fmoc-Met-Asp(OtBu)-OH (KD-1c) obtained as the DCHA salt in Example 2a hereinabove, in the presence of DIPEA (3.0 eq), EDC·HCl (2.0 eq), and HOBt·H$_2$O (2.0 eq) to afford the protected Foxy-5 derivative Fmoc-Met-Asp(OtBu)-Gly-Cys(Trt)-Glu(OtBu)-Leu-OtBu (SEQ_ID NO 4) in crude form. This was subsequently subjected to Fmoc deprotection with DBU in DCM followed by coupling with formic acid in the presence of EDC·HCl, HOBt·H$_2$O and DIPEA to yield For-Met-Asp(OtBu)-Gly-Cys(Trt)-Glu(OtBu)-Leu-OtBu (SEQ_ID NO 15). This protected hexapeptide was globally deprotected (Trt and tBu groups) by dissolution and stirring in a cocktail of TFA/(i-Pr)$_3$SiH/DTT. After completion of reaction, the crude product was obtained as a solid by precipitation with THF/MTBE. Chromatographic purification afforded the desired hexapeptide For-Met-Asp-Gly-Cys-Glu-Leu-OH (Foxy-5) in >90% yield and app 97% purity.
3+3 Route

Example 6—Preparation of Fragment KT-1 and KT-1*(for-Met-Asp(OtBu)-Gly-OH and Fmoc-Met-Asp(OtBu)-Gly-OH, Respectively)

Example 6a Example Using Fmoc-Methionine[1] in Place of Formyl-Methionine in the Preparation of Tripeptide KT-1* (Fmoc-Met-Asp(OtBu)-Gly-OH).

[1] To allow for optional later introduction of the formyl group.

Glycine methyl ester (25 gr) was reacted in DMF with Fmoc-Asp(OtBu)-OH in the presence of DIPEA (1.0 eq), EDAC, HCl (2.0 eq), and HOBt (2.0 eq). After standard work-up the crude product was purified on silica gel using 15% EtOAc/n-Hexane. 1 gr hereof was coupled with Fmoc-Met to afford protected tripeptide Fmoc-Met-Asp(OtBu)-Gly-OMe (2.0 gr, 72.7%). Identity confirmed by $^1$H NMR and mass spectometry.

Example 6b Preparation of Fragment KT-1 (for-Met-Asp(OtBu)-Gly-OH).

Glycine methyl ester was coupled with Fmoc-Asp(OtBu)-OH according to the procedure outlined in example 6a to afford protected dipeptide Fmoc-Asp(OtBu)-Gly-OMe. Fmoc deprotection hereof was achieved with DBU and coupling with commercially available For-Met-OH in DCM in the presence of DIPEA (LO eq), EDAC, HCl (2.0 eq), and HOBt (2.0 eq) affords desired fragment KT-1.

Example 7—Preparation of Fragment KT-2 (Fmoc-Cys(Trt)Glu(OtBu)-Leu-OMe)

Fmoc Leucine (250 gr) was dissolved in methanol and converted to Fmoc methyl leucinate in quantitative yield by treatment with thionyl chloride. Fmoc deprotection with DBU in dichloromethane afforded desired Leucine methyl ester (76 gr, 74% overall yield). Identity confirmed by $^1$H NMR and mass spectometry. Next, coupling of 10 gr Leucine methyl ester with Fmoc-Glu-(OtBu) in dichloromethane at high dilution in the presence of EDAC, HCl (2.0 eq), and HOBt (2.0 eq) at initially 0-5° C. for 1 hr followed by 15-20° C. for 1 hr afforded dipeptide Fmoc-Glu-(OtBu)-Leu-OMe (7.2 gr, 55% overall yield). Identity confirmed by $^1$H NMR and mass spectometry. For reaction with Fmoc cysteine in the next step, product isolation was omitted and the dichloromethane solution used directly after aqueous workup. The subsequent reaction of obtained dipeptide Fmoc-Glu-(OtBu)-Leu-OMe was thus performed using the dichloromethane solution referred to above. Fmoc deprotection was achieved with DBU and coupling with Fmoc-Cys(Trt)-OH in the presence of EDAC, HCl (1.2 eq), and HOBt (1.2 eq) afforded fragment KT-2 Fmoc-Cys(Trt)-Glu-(OtBu)-Leu-OMe (6.6 gr, 88% overall yield over two coupling reactions). Identity confirmed by $^1$H NMR and mass spectometry.

Example 8—Preparation of Alternative Tripeptide Fragment Fmoc-Cys(Trt)Glu(OtBu)-Leu-OtBu (KT-2*)

50 gr t-butyl Leucinate.HCl was coupled with 1.3 eq Fmoc-Glu-(OtBu) in dichloromethane at high dilution (50 vol) in the presence of EDAC, HCl (2.0 eq), and HOBt (2.0 eq) and DIPEA (5.0 eq) at initially 0-5° C. for 1 hr followed by 15-20° C. for 1 hr afforded dipeptide Fmoc-Glu-(OtBu)-Leu-OtBu (KD-3c). Identity was confirmed by $^1$H NMR and mass spectometry. For reaction with Fmoc-Cys(Trt)-OH in the next step, product isolation was omitted and the dichloromethane solution used directly after aqueous workup. The subsequent reaction of obtained dipeptide KD-3c was thus performed using the dichloromethane solution referred to above. Fmoc deprotection was achieved with DBU and coupling with 1.3 eq Fmoc-Cys(Trt)-OH in the presence of EDAC, HCl (1.2 eq), HOBt (1.2 eq) and DIPEA (5 eq) afforded the crude tripeptide KT-2*, which was purified by chromatography over silica gel (100-200) using EtOAc-hexane as eluent to furnish the tripeptide KT-2* Fmoc-Cys(Trt)Glu(OtBu)-Leu-OtBu as a white color solid (148 gr, 68% overall yield over two coupling reactions). Identity confirmed by 1H NMR and mass spectometry.

The above telescoped reactions were repeated from 75 gr 1-butyl Leucinate.HCl to furnish 208 gr KT-2*

Example 9a—Preparation of Foxy-5 by Coupling of Tripeptide Fragment KT-1 and KT-2 Followed by Deprotection Synthesis of Foxy-5 from the two tripeptide fragments, KT-1 and KT-2, is realized beginning with the Fmoc-deprotection of KT-2. Subsequent coupling with KT-1 affords For-Met-Asp(OtBu)-Gly-Cys(Trt)-Glu(OtBu)-Leu-OMe. Then saponification under basic conditions yields For-Met-Asp(OtBu)-Gly-Cys(Trt)-Glu(OtBu)-Leu-OH, and the latter upon deprotection of O-tBu and trityl protecting groups gives the desired hexapeptide Foxy-5 in crude form.

Example 9b—Preparation of Foxy-5 by Coupling of Tripeptide Fragment KT-1* and KT-2* Followed by Fmoc Removal, Formylation and Deprotection Synthesis of Foxy-5 from the two tripeptide fragments, KT-1* and KT-2*, is realized beginning with the Fmoc-deprotection of KT-2*. Subsequent coupling with KT-1* affords Fmoc-Met-Asp(OtBu)-Gly-Cys(Trt)-Glu(OtBu)-Leu-OtBu (SEQ_ID NO 4) which was subsequently subjected to Fmoc deprotection with DBU in DCM followed by coupling with formic acid in the presence of EDC·HCl, HOBt·H$_2$O and DIPEA to yield For-Met-Asp(OtBu)-Gly-Cys(Trt)-Glu(OtBu)-Leu-OtBu (SEQ_ID NO 15). This protected hexapeptide was globally deprotected (Trt and tBu groups) by dissolution and stirring in a cocktail of TFA/(i-Pr)$_3$SiH/DTT. After completion of reaction, the crude product was obtained as a solid by precipitation with THF/MTBE. Chromatographic purification afforded the desired hexapeptide For-Met-Asp-Gly-Cys-Glu-Leu-OH (Foxy-5) in >90% yield and app. 97% purity.
4+1+1 Route

Example 10 Preparation of Foxy-5 by Sequential Coupling of Tetrapeptide Fmoc-Gly-Cys(Trt)-Glu(OtBu)-Leu-OtBu (SEQ_ID NO 6) with Fmoc-Asp-OtBu and Fmoc-Met Followed by Fmoc Removal, Formylation and Deprotection Fmoc-Gly-Cys(Trt)-Glu(OtBu)-Leu-OtBu (SEQ_ID NO 6) as obtained hereinabove in Example 4a was first reacted with DBU to achieve Fmoc deprotection. Before proceeding with the next coupling step, the reaction mass was passed through a silica plug to remove DBU, which has been found in previous experiments to induce formation of an undesired aspartimide by-product. Removal of DBU before coupling with Fmoc-Asp-OtBu effectively suppresses the aspartimide formation. After silica plug treatment the DCM solution was reacted with Fmoc-Asp(OtBu) in the presence of DIPEA, EDAC, HCl (1.2 eq), and HOBt (1.2 eq) to afford protected pentapeptide Fmoc-Asp(OtBu)-Gly-Cys(Trt)-Glu(OtBu)-Leu-OtBu (SEQ_ID NO 3). Product identity was confirmed by $^1$H NMR and mass spectometry.

Fmoc deprotection of the obtained pentapeptide Fmoc-Asp(OtBu)-Gly-Cys(Trt)-Glu(OtBu)-Leu-OtBu (SEQ_ID NO 3) was achieved with DBU, and coupling with Fmoc-Met in DCM-THF (50 vol+10 vol) as solvent in the presence of DIPEA (3.0 eq), EDC·HCl (2.0 eq), and HOBt·H$_2$O (2.0 eq) afforded the protected hexapeptide Fmoc-Met-Asp(OtBu)-Gly-Cys(Trt)-Glu(OtBu)-Leu-OtBu (SEQ_ID NO 4) in crude form.

Fmoc deprotection of the obtained hexapeptide Fmoc-Met-Asp(OtBu)-Gly-Cys(Trt)-Glu(OtBu)-Leu-OtBu_(SEQ_ID NO 4) from Example 4 was achieved with DBU in DCM (50 vol) followed by coupling with formic acid (3.0 eq) in the presence of EDC·HCl (4.0 eq), HOBt·H$_2$O (4.0 eq) and DIPEA (4.0 eq) to yield For-Met-Asp(OtBu)-Gly-Cys(Trt)-Glu(OtBu)-Leu-OtBu (SEQ_ID NO 15), which was globally deprotected (Trt and tBu groups) by dissolution and stirring in a cocktail of TFA (10 vol)/(i-Pr)$_3$SiH (TIS, 1.7 vol)/DTT (1.7 eq) for 1.5 hrs. After completion of reaction, the crude product was obtained as a solid in 97% yield (9.5 gr) by precipitation with THF/MTBE. Chromatographic purification afforded the desired hexapeptide For-Met-Asp-Gly-Cys-Glu-Leu-OH (Foxy-5) in 97.6% purity.

3+1+1+1 Route

Example 11 Feasibility of Linear Solution Phase Approach Towards Foxy-5

KT-2 (Fmoc-Cys(Trt)Glu(OtBu)-Leu-OMe) as obtained hereinabove was reacted with DBU in DCM to achieve Fmoc deprotection, and subsequently with Fmoc-Gly-OH in the presence of DIPEA, EDAC, HCl (1.2 eq), and HOBt (1.2 eq) to afford protected tetrapeptide Fmoc-Gly-Cys(Trt)-Glu(OtBu)-Leu-OMe (SEQ_ID NO 7). Product identity was confirmed by by $^1$H NMR and mass spectometry. The crude product was further reacted in analogous fashion with DBU in DCM to achieve Fmoc deprotection and subsequently with Fmoc-Asp(OtBu) in the presence of DIPEA, EDAC, HCl (1.2 eq), and HOBt (1.2 eq) to afford protected pentapeptide Fmoc-Asp(OtBu)-Gly-Cys(Trt)-Glu(OtBu)-Leu-OMe (SEQ_ID NO 9), which was obtained as a white solid after silica gel purification and slurrying in methanol. Product identity was confirmed by by $^1$H NMR and mass spectometry. Fmoc deprotection of the obtained pentapeptide is achieved with DBU and coupling with commercially available For-Met-OH in DCM in the presence of DIPEA (1.0 eq), EDAC, HCl (2.0 eq), and HOBt (2.0 eq) affords the protected Foxy-5 derivative For-Met-Asp(OtBu)-Gly-Cys(Trt)-Glu(OtBu)-Leu-OMe (SEQ_ID NO 3), which upon saponification under basic conditions yields For-Met-Asp(OtBu)-Gly-Cys(Trt)-Glu(OtBu)-Leu-OH (SEQ_ID NO 4), and the latter upon deprotection of O-tBu and trityl protecting groups gives the desired hexapeptide Foxy-5 in crude form.

Example 12
Fmoc-Gly-Cys(Trt)Glu(OtBu)-Leu-OtBu (SEQ ID NO 6)

KT-2* (Fmoc-Cys(Trt)Glu(OtBu)-Leu-OtBu) as obtained in Example 8 hereinabove was reacted with DBU in DCM (50 vol) to achieve Fmoc deprotection, and subsequently reacted with 1.3 eq. Fmoc-Gly-OH in the presence of DIPEA (3 eq), EDC·HCl (2.0 eq), and HOBt (2.0 eq) to afford protected tetrapeptide Fmoc-Gly-Cys(Trt)-Glu(OtBu)-Leu-OtBu (SEQ_ID NO 6). Good conversion was observed by TLC, and the DCM layer was washed with water and brine. The final organic layer was concentrated to 10-15 vol and used as such in the next stage without isolation.

Example 13—Fmoc-Asp(OtBu)-Gly-Cys(Trt)Glu(OtBu)-Leu-OtBu (SEQ ID NO 10)

Fmoc-Gly-Cys(Trt)-Glu(OtBu)-Leu-OtBu (SEQ_ID NO 6) as obtained hereinabove as a concentrated DCM solution was first reacted with DBU to achieve Fmoc deprotection. Before proceeding with the next coupling step, the reaction mass was passed through a silica plug to remove DBU, which has been found in previous experiments to induce formation of an undesired aspartimide by-product. Removal of DBU before coupling with Fmoc-Asp-OtBu effectively suppresses the aspartimide formation. After silica plug treatment the DCM solution was reacted with Fmoc-Asp(OtBu) in the presence of DIPEA, EDAC, HCl (1.2 eq), and HOBt (1.2 eq) to afford protected pentapeptide Fmoc-Asp(OtBu)-Gly-Cys(Trt)-Glu(OtBu)-Leu-OtBu (SEQ_ID NO 3). Product identity was confirmed by by $^1$H NMR and mass spectometry.

The telescoped reactions were repeated twice starting from 148 gr and 220 gr starting material, affording 107 and 163 gr product, respectively (58.1% and 59.2% of theory). Example 14—Fmoc-Met-Asp(OtBu)-Gly-Cys(Trt)-Glu(OtBu)-Leu-OtBu (SEQ ID NO 4) Fmoc deprotection of the obtained pentapeptide Fmoc-Asp(OtBu)-Gly-Cys(Trt)Glu(OtBu)-Leu-OtBu (SEQ ID NO 10) from Example 13 was achieved with DBU, and coupling with Fmoc-Met in DCM-THF (50 vol+10 vol) as solvent in the presence of DIPEA (3.0 eq), EDC·HCl (2.0 eq), and HOBt·H$_2$O (2.0 eq) afforded the protected Foxy-5 derivative Fmoc-Met-Asp(OtBu)-Gly-Cys(Trt)-Glu(OtBu)-Leu-OtBu (SEQ_ID NO 4) in crude form. Purification was performed by column chromatography using DCM/THF as eluent. The purified product was slurried in DIPE to afford a white colored solid.

The purification was performed several times under various conditions, such as precipitation with anti-solvents and chromatography. The best solution was found to be column chromatography followed by slurrying in DIPE, which on 25 gr scale gave yields of 78% and 95.4% chemical purity.

Example 15 for-Met-Asp(OtBu)-Gly-Cys(Trt)-Glu(OtBu)-Leu-OtBu, (SEQ_ID NO 15)

Fmoc deprotection of the obtained hexapeptide Fmoc-Met-Asp(OtBu)-Gly-Cys(Trt)-Glu(OtBu)-Leu-OtBu (SEQ ID NO 4) from Example 14 was achieved with DBU in DCM (50 vol) followed by coupling with formic acid (3.0 eq) in the presence of EDC·HCl (4.0 eq), HOBt·H$_2$O (4.0 eq) and DIPEA (4.0 eq) to yield For-Met-Asp(OtBu)-Gly-Cys(Trt)-Glu(OtBu)-Leu-OtBu (SEQ_NO 15).

The reaction was performed three times from 4, 18 and 18 gr starting material, respectively, to afford yields of 75-83% and chemical purities of between 67.5-77.2%.

Example 16 for-Met-Asp-Gly-Cys-Glu-Leu-OH (Foxy-5), (SEQ ID NO 1)

14 gr of the obtained hexapeptide from Example 15 was globally deprotected (Trt and tBu groups) by dissolution and stirring in a cocktail of TFA (10 vol)/(i-Pr)$_3$SiH (TIS, 1.7 vol)/DTT (1.7 eq) for 1.5 hrs. After completion of reaction, the crude product was obtained as a solid in 97% yield (9.5 gr) by precipitation with THF/MTBE. Chromatographic purification afforded the desired hexapeptide For-Met-Asp-Gly-Cys-Glu-Leu-OH (Foxy-5) in 97.6% purity.

The invention claimed is:

1. A composition comprising a protected peptide selected from
   a. $PG_1$-Gly-Cys($PG_2$)-Glu($OPG_3$)-Leu-$OR_1$
   b. $PG_1$-Asp($OPG_3$)-Gly-Cys($PG_2$)-Glu($OPG_3$)-Leu-$OR_1$
   c. $PG_1$-Met-Asp($OPG_3$)-Gly-Cys($PG_2$)-Glu($OPG_3$)-Leu-$OR_1$
   d. For-Met-Asp($OPG_3$)-Gly-Cys($PG_2$)-Glu($OPG_3$)-Leu-$OR_1$,
   wherein $PG_1$ is selected from H and a base sensitive protecting group, $PG_2$ is selected from H and trityl (Trt), $PG_3$ is selected from H and tert-butyl (tBu), and $R_1$ is chosen from H and $C_1$-$C_6$ alkyl with the proviso that $PG_1$, $PG_2$, $PG_3$ and $R_1$ are not simultaneously hydrogen and
   wherein the composition is free of peptides that have an aspartimide moiety.

2. The composition of claim 1, wherein the protected peptide is selected from
   a. Fmoc-Gly-Cys(Trt)-Glu(OtBu)-Leu-OtBu (SEQ ID NO: 6),
   b. Fmoc-Asp(OtBu)-Gly-Cys(Trt)-Glu(OtBu)-Leu-OtBu (SEQ ID NO: 3)
   c. Fmoc-Met-Asp(OtBu)-Gly-Cys(Trt)-Glu(OtBu)-Leu-OtBu (SEQ ID NO: 4)
   d. For-Met-Asp(OtBu)-Gly-Cys(Trt)-Glu(OtBu)-Leu-OtBu (SEQ ID NO: 15).

3. The composition of claim 1, wherein the protected peptide is in solid form.

4. The composition of claim 1, wherein the protected peptide is in crystalline form.

5. The composition according to claim 1, wherein $PG_1$ is fluorenylmethyloxycarbonyl (Fmoc).

6. The composition according to claim 1, wherein $R_1$ is methyl, ethyl or tert-butyl (tBu).

* * * * *

SEQUENCE LISTING

```
<160> NUMBER OF SEQ ID NOS: 15

<210> SEQ ID NO 1
<211> LENGTH: 6
<212> TYPE: PRT
<213> ORGANISM: Artificial Sequence
<220> FEATURE:
<223> OTHER INFORMATION: Peptide
<220> FEATURE:
<221> NAME/KEY: MOD_RES
<222> LOCATION: (1)..(1)
<223> OTHER INFORMATION: Formyl-methionine

<400> SEQUENCE: 1

Met Asp Gly Cys Glu Leu
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: (Tert-Butoxycarbonyl)-methionine
<220> FEATURE:
<221> NAME/KEY: MOD_RES
<222> LOCATION: (2)..(2)
<223> OTHER INFORMATION: Aspartic acid tert-butylester
<220> FEATURE:
<221> NAME/KEY: MOD_RES
<222> LOCATION: (4)..(4)
<223> OTHER INFORMATION: Trityl-cystein
<220> FEATURE:
<221> NAME/KEY: MOD_RES
<222> LOCATION: (5)..(5)
<223> OTHER INFORMATION: Glutamic acid tert-butylester
<220> FEATURE:
<221> NAME/KEY: MOD_RES
<222> LOCATION: (6)..(6)
<223> OTHER INFORMATION: Leucine tert-butylester

<400> SEQUENCE: 2

Met Asp Gly Cys Glu Leu
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: (Fluorenylmethoxycarbonyl)-aspartic acid tert-
      butylester
<220> FEATURE:
<221> NAME/KEY: MOD_RES
<222> LOCATION: (3)..(3)
<223> OTHER INFORMATION: Trityl-cystein
<220> FEATURE:
<221> NAME/KEY: MOD_RES
<222> LOCATION: (4)..(4)
```

```
<223> OTHER INFORMATION: Glutamic acid tert-butylester
<220> FEATURE:
<221> NAME/KEY: MOD_RES
<222> LOCATION: (5)..(5)
<223> OTHER INFORMATION: Leucine tert-butylester

<400> SEQUENCE: 3

Asp Gly Cys Glu Leu
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Formyl-methionine
<220> FEATURE:
<221> NAME/KEY: MOD_RES
<222> LOCATION: (2)..(2)
<223> OTHER INFORMATION: Aspartic acid tert-butylester
<220> FEATURE:
<221> NAME/KEY: MOD_RES
<222> LOCATION: (4)..(4)
<223> OTHER INFORMATION: Trityl-cystein
<220> FEATURE:
<221> NAME/KEY: MOD_RES
<222> LOCATION: (5)..(5)
<223> OTHER INFORMATION: Glutamic acid tert-butylester
<220> FEATURE:
<221> NAME/KEY: MOD_RES
<222> LOCATION: (6)..(6)
<223> OTHER INFORMATION: Leucine tert-butylester

<400> SEQUENCE: 4

Met Asp Gly Cys Glu Leu
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Cysteine acetonide
<220> FEATURE:
<221> NAME/KEY: MOD_RES
<222> LOCATION: (3)..(3)
<223> OTHER INFORMATION: Glutamic acid tert-butylester
<220> FEATURE:
<221> NAME/KEY: MOD_RES
<222> LOCATION: (4)..(4)
<223> OTHER INFORMATION: Leucine tert-butylester

<400> SEQUENCE: 5

Gly Cys Glu Leu
1

<210> SEQ ID NO 6
<211> LENGTH: 4
<212> TYPE: PRT
<213> ORGANISM: Artificial Sequence
<220> FEATURE:
<223> OTHER INFORMATION: Synthetide peptide
<220> FEATURE:
<221> NAME/KEY: MOD_RES
<222> LOCATION: (1)..(1)
```

```
<223> OTHER INFORMATION: (Fluorenylmethoxycarbonyl)-glycine
<220> FEATURE:
<221> NAME/KEY: MOD_RES
<222> LOCATION: (2)..(2)
<223> OTHER INFORMATION: Trityl-cystein
<220> FEATURE:
<221> NAME/KEY: MOD_RES
<222> LOCATION: (3)..(3)
<223> OTHER INFORMATION: Glutamic acid tert-butylester
<220> FEATURE:
<221> NAME/KEY: MOD_RES
<222> LOCATION: (4)..(4)
<223> OTHER INFORMATION: Leucine tert-butylester

<400> SEQUENCE: 6

Gly Cys Glu Leu
1

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: (Fluorenylmethoxycarbonyl)-glycine
<220> FEATURE:
<221> NAME/KEY: MOD_RES
<222> LOCATION: (2)..(2)
<223> OTHER INFORMATION: Trityl-cystein
<220> FEATURE:
<221> NAME/KEY: MOD_RES
<222> LOCATION: (3)..(3)
<223> OTHER INFORMATION: Glutamic acid tert-butylester
<220> FEATURE:
<221> NAME/KEY: MOD_RES
<222> LOCATION: (4)..(4)
<223> OTHER INFORMATION: Leucine tert-butylester

<400> SEQUENCE: 7

Gly Cys Glu Leu
1

<210> SEQ ID NO 8
<211> LENGTH: 4
<212> TYPE: PRT
<213> ORGANISM: Artificial Sequence
<220> FEATURE:
<223> OTHER INFORMATION: Synthetic peptide

<400> SEQUENCE: 8

Gly Cys Glu Leu
1

<210> SEQ ID NO 9
<211> LENGTH: 5
<212> TYPE: PRT
<213> ORGANISM: Artificial Sequence
<220> FEATURE:
<223> OTHER INFORMATION: Synthetic sequence
<220> FEATURE:
<221> NAME/KEY: MOD_RES
<222> LOCATION: (1)..(1)
<223> OTHER INFORMATION: (Fluorenylmethoxycarbonyl)-aspartic acid tert-
      butylester
<220> FEATURE:
<221> NAME/KEY: MOD_RES
<222> LOCATION: (3)..(3)
<223> OTHER INFORMATION: Trityl-cystein
<220> FEATURE:
<221> NAME/KEY: MOD_RES
```

```
<222> LOCATION: (4)..(4)
<223> OTHER INFORMATION: Glutamic acid tert-butylester
<220> FEATURE:
<221> NAME/KEY: MOD_RES
<222> LOCATION: (5)..(5)
<223> OTHER INFORMATION: Leucine-methylester

<400> SEQUENCE: 9

Asp Gly Cys Glu Leu
1               5

<210> SEQ ID NO 10
<211> LENGTH: 5
<212> TYPE: PRT
<213> ORGANISM: Artificial Sequence
<220> FEATURE:
<223> OTHER INFORMATION: Syntheti peptide
<220> FEATURE:
<221> NAME/KEY: MOD_RES
<222> LOCATION: (1)..(1)
<223> OTHER INFORMATION: (Fluorenylmethoxycarbonyl)-aspartic acid tert-
      butylester
<220> FEATURE:
<221> NAME/KEY: MOD_RES
<222> LOCATION: (3)..(3)
<223> OTHER INFORMATION: Trityl-cystein
<220> FEATURE:
<221> NAME/KEY: MOD_RES
<222> LOCATION: (4)..(4)
<223> OTHER INFORMATION: Glutamic acid tert-butylester
<220> FEATURE:
<221> NAME/KEY: MOD_RES
<222> LOCATION: (5)..(5)
<223> OTHER INFORMATION: Leucine-methylester

<400> SEQUENCE: 10

Asp Gly Cys Glu Leu
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic peptide

<400> SEQUENCE: 11

Met Asp Gly Cys Cys
1               5

<210> SEQ ID NO 12
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Carboxybenzyl-methionine
<220> FEATURE:
<221> NAME/KEY: MOD_RES
<222> LOCATION: (2)..(2)
<223> OTHER INFORMATION: Aspartic acid benzylester
<220> FEATURE:
<221> NAME/KEY: MOD_RES
<222> LOCATION: (4)..(4)
<223> OTHER INFORMATION: Benzylcysteine

<400> SEQUENCE: 12

Met Asp Gly Cys
1
```

<210> SEQ ID NO 13
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Carboxybenzyl-methionine
<220> FEATURE:
<221> NAME/KEY: MOD_RES
<222> LOCATION: (2)..(2)
<223> OTHER INFORMATION: Aspartic acid benzylester
<220> FEATURE:
<221> NAME/KEY: MOD_RES
<222> LOCATION: (4)..(4)
<223> OTHER INFORMATION: Benzylcysteine
<220> FEATURE:
<221> NAME/KEY: MOD_RES
<222> LOCATION: (5)..(5)
<223> OTHER INFORMATION: Glutamic acid benzylester
<220> FEATURE:
<221> NAME/KEY: MOD_RES
<222> LOCATION: (6)..(6)
<223> OTHER INFORMATION: Leucine benzylester

<400> SEQUENCE: 13

Met Asp Gly Cys Glu Leu
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide

<400> SEQUENCE: 14

Met Asp Gly Cys Glu Leu
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: (Tert-Butoxycarbonyl)-methionine
<220> FEATURE:
<221> NAME/KEY: MOD_RES
<222> LOCATION: (2)..(2)
<223> OTHER INFORMATION: Aspartic acid tert-butylester
<220> FEATURE:
<221> NAME/KEY: MOD_RES
<222> LOCATION: (4)..(4)
<223> OTHER INFORMATION: Trityl-cystein
<220> FEATURE:
<221> NAME/KEY: MOD_RES
<222> LOCATION: (5)..(5)
<223> OTHER INFORMATION: Glutamic acid tert-butylester

```
<220> FEATURE:
<221> NAME/KEY: MOD_RES
<222> LOCATION: (6)..(6)
<223> OTHER INFORMATION: Leucine tert-butylester

<400> SEQUENCE: 15

Met Asp Gly Cys Glu Leu
1               5
```